United States Patent
Hepp et al.

(10) Patent No.: US 7,251,524 B1
(45) Date of Patent: *Jul. 31, 2007

(54) APPARATUS AND METHOD FOR DETERMINING CARDIAC OUTPUT IN A LIVING SUBJECT

(75) Inventors: Dennis G. Hepp, Coon Rapids, MN (US); Gail D. Baura, San Diego, CA (US); James O. Elf, San Diego, CA (US); Jeremy Robert Malecha, San Diego, CA (US); Sau Kuen Ng, Hoboken, NJ (US)

(73) Assignee: Cardiodynamics International Corporation, San Diego, CA (US)

( * ) Notice: Subject to any disclaimer, the term of this patent is extended or adjusted under 35 U.S.C. 154(b) by 368 days.

This patent is subject to a terminal disclaimer.

(21) Appl. No.: 10/616,126

(22) Filed: Jul. 8, 2003

Related U.S. Application Data

(63) Continuation of application No. 09/903,473, filed on Jul. 10, 2001, now Pat. No. 6,602,201, which is a continuation-in-part of application No. 09/613,183, filed on Jul. 10, 2000, now Pat. No. 6,636,754.

(51) Int. Cl.
*A61B 5/04* (2006.01)
(52) U.S. Cl. .................................... 600/513
(58) Field of Classification Search ............ 600/509, 600/513, 521
See application file for complete search history.

(56) References Cited

U.S. PATENT DOCUMENTS

RE30,101 E    9/1979  Kubicek et al.

| 4,577,639 A | 3/1986 | Simon et al. |
| 5,103,828 A | 4/1992 | Sramek |
| 5,178,151 A | 1/1993 | Sackner |
| 5,178,154 A | 1/1993 | Ackmann et al. |
| 5,184,620 A | 2/1993 | Cudahy et al. |
| 5,287,520 A | 2/1994 | Kaiser |

(Continued)

FOREIGN PATENT DOCUMENTS

EP    0776631    4/1997

(Continued)

OTHER PUBLICATIONS

CardioDynamics International Corporation Information Sheets for BioZ.com, (6 pages), no date, www.bioz.com.

(Continued)

*Primary Examiner*—Scott M. Getzow
(74) *Attorney, Agent, or Firm*—Gazdzinski & Associates

(57) ABSTRACT

An improved apparatus and method for determining the cardiac output of a living subject. The improved apparatus generally comprises one or more electrode assemblies or patches affixed to the skin of the subject in the vicinity of the thoracic cavity. In one embodiment, the apparatus comprises a constant current source impedance cardiography (ICG) monitor adapted as a stand-alone system. In another embodiment, the apparatus comprises a module adapted for use with a host monitoring system, the latter providing ECG, blood pressure, and/or other inputs to the module. Method of detecting a loss of electrical continuity in one or more of the terminals of the electrode patch, and selecting between a plurality of signal inputs based on signal quality, are also disclosed.

53 Claims, 33 Drawing Sheets

U.S. PATENT DOCUMENTS

| | | | |
|---|---|---|---|
| 5,505,209 | A | 4/1996 | Reining |
| 5,511,553 | A | 4/1996 | Segalowitz |
| 5,576,952 | A * | 11/1996 | Stutman et al. ............. 600/300 |
| 5,590,648 | A | 1/1997 | Mitchell et al. |
| 5,876,351 | A | 3/1999 | Rohde |
| 5,895,298 | A | 4/1999 | Faupel et al. |
| 6,016,445 | A | 1/2000 | Baura |
| 6,135,966 | A * | 10/2000 | Ko ............................ 600/481 |
| 6,141,575 | A | 10/2000 | Price |
| 6,186,955 | B1 | 2/2001 | Baura |
| 6,217,525 | B1 | 4/2001 | Medema et al. |
| 6,246,907 | B1 * | 6/2001 | Lin et al. ....................... 607/5 |
| 6,561,986 | B2 | 5/2003 | Baura et al. |
| 6,671,540 | B1 * | 12/2003 | Hochman ................... 600/431 |
| 6,820,049 | B1 * | 11/2004 | Monroe et al. ............... 703/21 |

FOREIGN PATENT DOCUMENTS

| | | |
|---|---|---|
| WO | WO 9853737 | 12/1998 |
| WO | WO 0062684 | 10/2000 |

OTHER PUBLICATIONS

CardioDynamics' Technology Information Sheets for "Thoracic Electrical Bioimpedance (TEB)", (7 pages), no date, www.cardiodynamics.com.

CardioDynamics BioZ Information Sheets for "The BioZ System", (8 pages), no date, www.cardiodynamics.com.

W. G. Kubicek, Ph.D., et al., "Development and Evaluation of an Impedance Cardiac Output System", Acrospace Medicine, pp. 1208-1212, Dec. 1966.

Jan Nybor, Sc.D., M.D., et al., "Electrical Impedance Plethysmography", Circulation, vol. II, pp. 811-821, Dec. 1950.

ConMed Coporation POSITRACE ECG Electrode (Exhibit "A" consisting of five pages), Jun. 1998.

G. W. N. Dalzell, et al., "Initial Experience with a Microprocessor Controlled Current Based Defibrillator," University of Ulster, Jordanstown, and Regional Medical Cardiology Centre, Royal Victoria Hospital, Belfast, Ireland, pp. 502-505, Feb. 2, 1989.

B. Bo Sramek, MSEE, "Hemodynamic and Pump-Performance Monitoring by Electrical Bioimpedance," Problem in Respiratory Care, vol. 2, No. 2, pp. 274-290, Apr./Jun. 1989.

G. D. Baura, Ph.D., et al., "Intra-Sensor Spacing and Sensor Placement Variability on Impedance Cardiography (ICG) Parameters," CDIC Technical Report #TR-048, consisting of 2 pages, Jul. 26, 2000.

GE Medical Systems Information Technologies, "Non-Invasive Hemodynamic Monitoring With BioZ Impedance Cardiography," consisting of 2 pages, 2001.

Wantagh, Incorporated, "Noninvasive Continuous Hemodynamic Patient Monitoring System—Operator'Manual," Title page, plus pp. 1-42 (date unknown).

Wantagh, Incorporated, "Noninvasive Continuous Hemodynamic Monitoring," pp. 1-4 (date unknown).

Lead-Lok, Inc., (Aug. 8, 1998), Final Production Specifications consisitng of two (2) pages.

Sorba Medical Systems—product literature entitled "Transthoracic Electrical Bioimpedance R-ware Triggered Ensemble" Averaging consisitng of four (4) pages.

Sorba Medical Systems—product literature regarding the CIC-1000™—consisting of two (2) pages.

Sorba Medical Systems—product literature regarding the Steorra™ impedance cardiograph—consisting of three (3) pages.

Solar®8000M Patient Monitor *GE Medical Systems* web page (6 pages).

Non-Invasive Hemodynamic Monitoring with BioZ® Impedance Cardiography web page (2 pages).

* cited by examiner

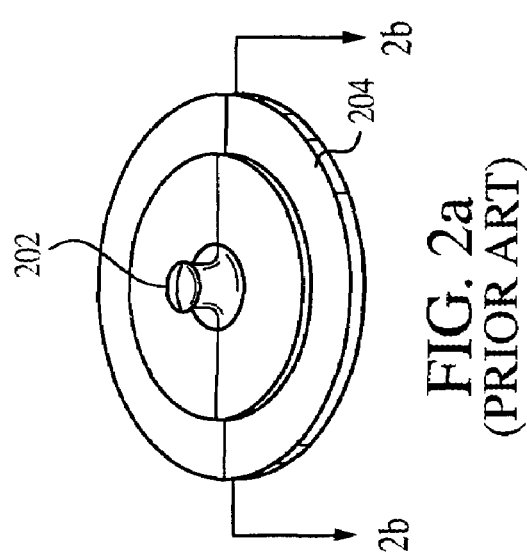
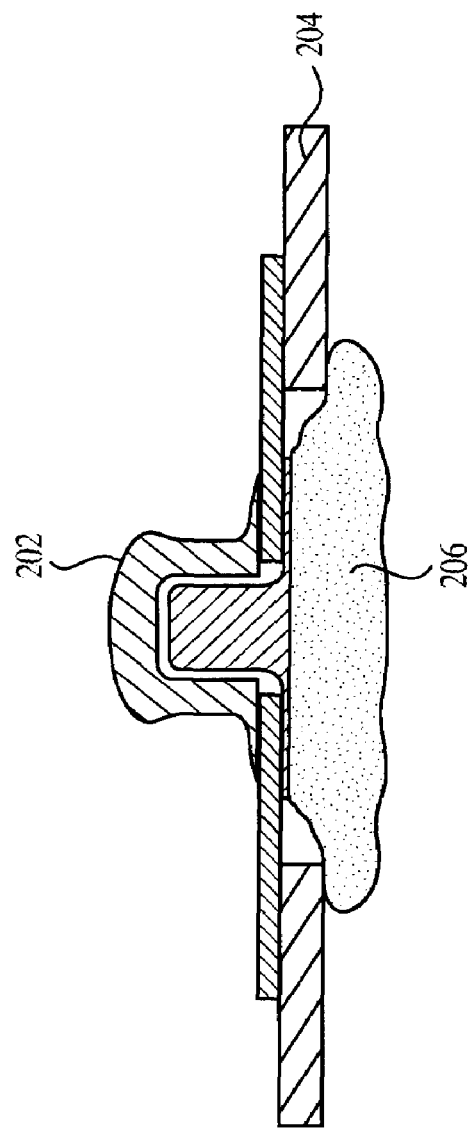
FIG. 2a (PRIOR ART)
FIG. 2b (PRIOR ART)

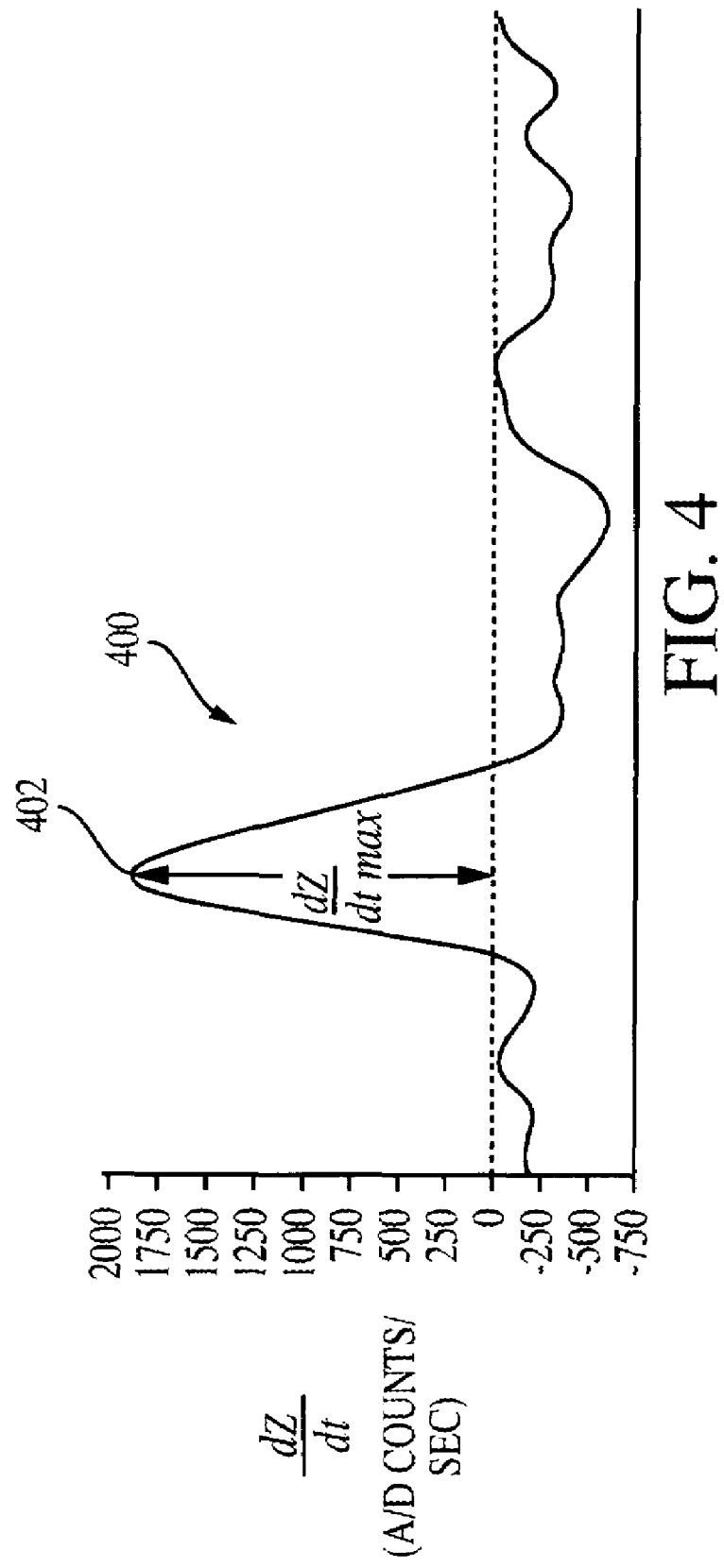

(PART 1 OF 2)

(PART 2 OF 2)

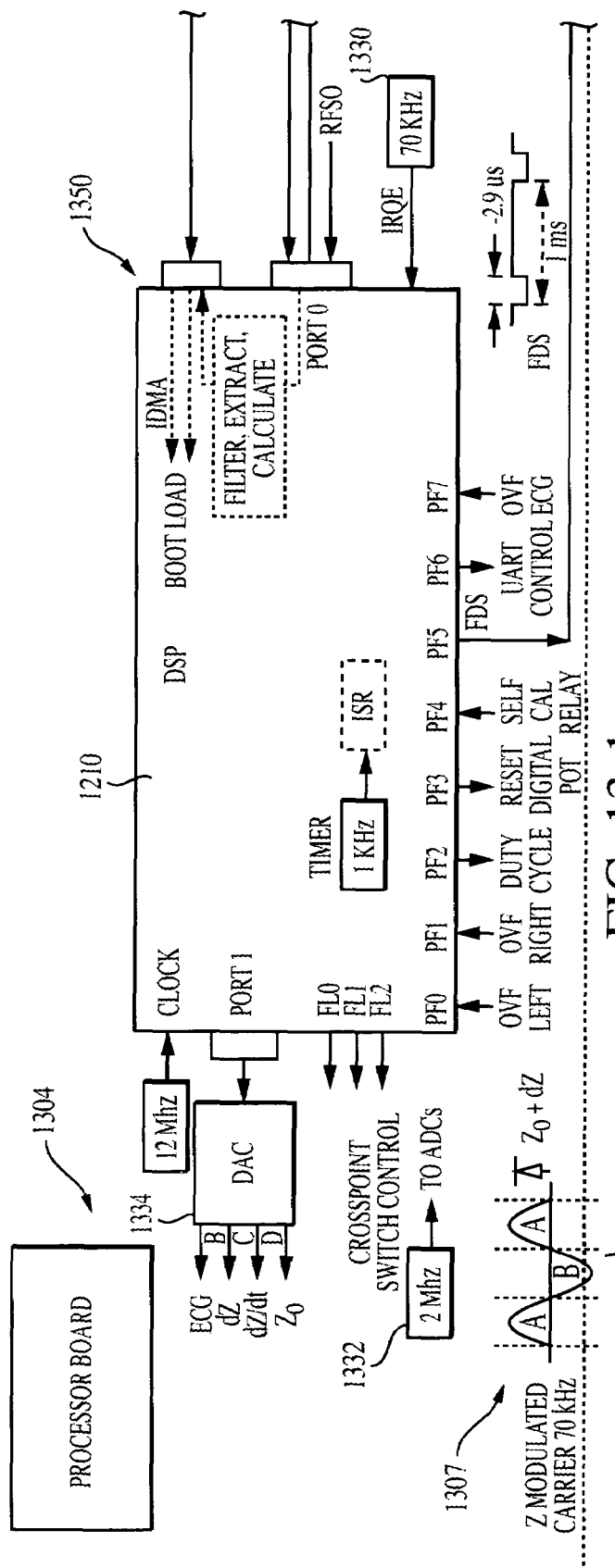

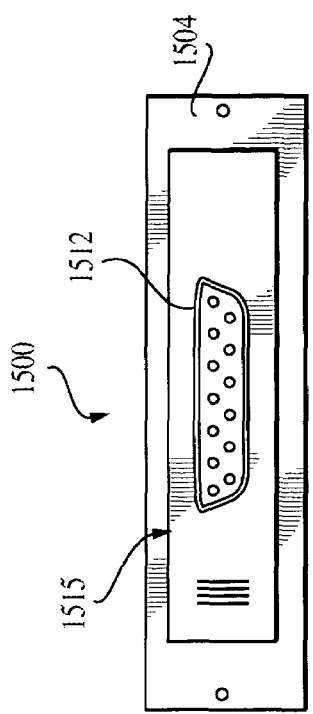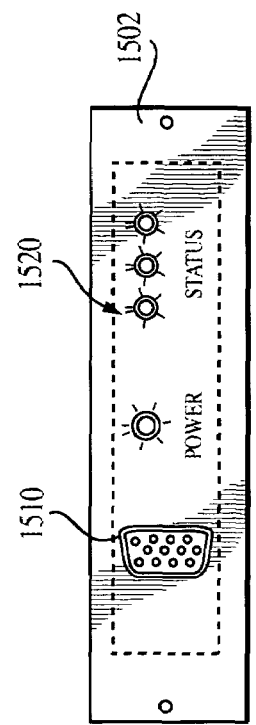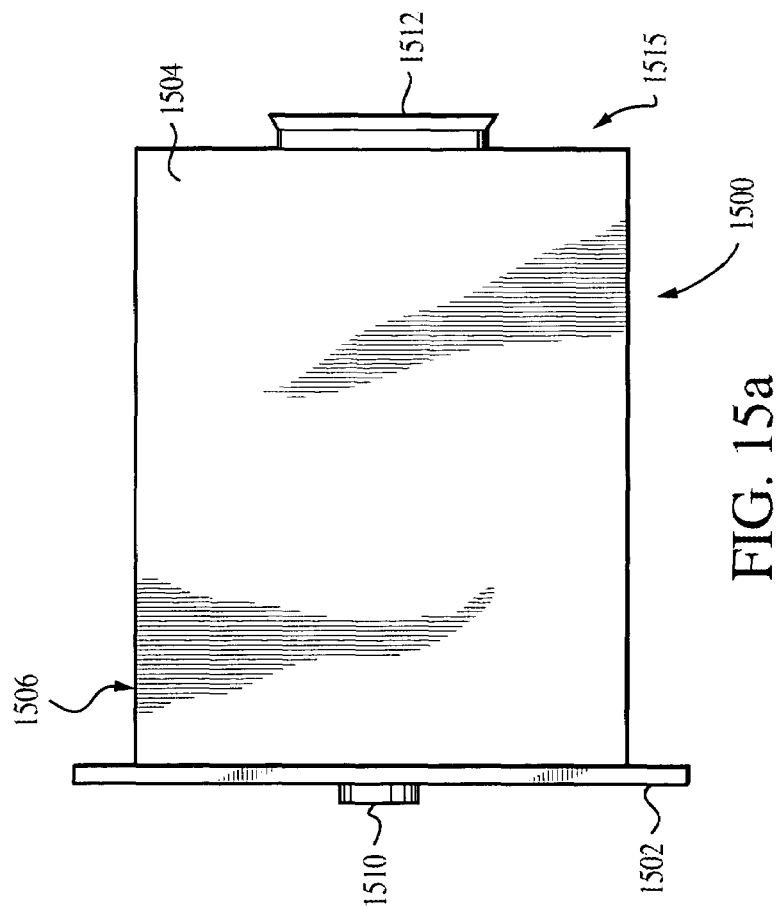

APPARATUS AND METHOD FOR DETERMINING CARDIAC OUTPUT IN A LIVING SUBJECT

This application is a continuation of U.S. patent application Ser. No. 09/903,473 entitled "Apparatus And Method For Determining Cardiac Output In A Living Subject" filed Jul. 10, 2001, now U.S. Pat. No. 6,602,201, which is a continuation-in-part of U.S. patent application Ser. No. 09/613,183 entitled "Apparatus And Method For Determining Cardiac Output In A Living Subject" filed Jul. 10, 2000, now U.S. Pat. No. 6,636,754, both assigned to the Assignee hereof and incorporated by reference herein in their entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

RELATED APPLICATIONS

This application is related to co-pending U.S. patent application Ser. No. 09/764,589 entitled "Method And Apparatus For Hemodynamic Assessment Including Fiducial Point Detection" filed Jan. 17, 2001, and assigned to the Assignee hereof, which is incorporated by reference herein in its entirety.

BACKGROUND OF THE INVENTION

1. Field of the Invention

The present invention relates generally to the field of biomedical analysis, and particularly to an apparatus and method for non-invasively determining the cardiac output in a living subject using impedance cardiography.

2. Description of Related Technology

Noninvasive estimates of cardiac output (CO) can be obtained using impedance cardiography. Strictly speaking, impedance cardiography, also known as thoracic bioimpedance or impedance plethysmography, is used to measure the stroke volume of the heart. As shown in Eqn. (1), when the stroke volume is multiplied by heart rate, cardiac output is obtained.

$$CO = \text{stroke volume} \times \text{heart rate.} \quad (1)$$

The heart rate is obtained from an electrocardiogram. The basic method of correlating thoracic, or chest cavity, impedance, $Z_T(t)$, with stroke volume was developed by Kubicek, et al. at the University of Minnesota for use by NASA. See, e.g., U.S. Reissue Pat. No. 30,101 entitled "Impedance plethysmograph" issued Sep. 25, 1979, which is incorporated herein by reference in its entirety. The method generally comprises modeling the thoracic impedance $Z_T(t)$ as a constant impedance, $Z_o$, and time-varying impedance, $\Delta Z$(t), as illustrated schematically in FIG. 1. The time-varying impedance is measured by way of an impedance waveform derived from electrodes placed on various locations of the subject's thorax; changes in the impedance over time can then be related to the change in fluidic volume (i.e., stroke volume), and ultimately cardiac output via Eqn. (1) above.

Despite their general utility, prior art impedance cardiography techniques such as those developed by Kubicek, et al. have suffered from certain disabilities. First, the distance (and orientation) between the terminals of the electrodes of the cardiography device which are placed on the skin of the subject is highly variable; this variability introduces error into the impedance measurements. Specifically, under the prior art approaches, individual electrodes 200 such as that shown in FIGS. 2a and 2b, which typically include a button "snap" type connector 202, compliant substrate 204, and gel electrolyte 206 are affixed to the skin of the subject at locations determined by the clinician. Since there is no direct physical coupling between the individual electrodes, their placement is somewhat arbitrary, both with respect to the subject and with respect to each other. Hence, two measurements of the same subject by the same clinician may produce different results, dependent at least in part on the clinician's choice of placement location for the electrodes. It has further been shown that with respect to impedance cardiography measurements, certain values of electrode spacing yield better results than other values.

Additionally, as the subject moves, contorts, and/or respirates during the measurement, the relative orientation and position of the individual electrodes may vary significantly. Electrodes utilizing a weak adhesive may also be displaced laterally to a different location on the skin through subject movement, tension on the electrical leads connected to the electrodes, or even incidental contact. This so-called "motion artifact" can also reflect itself as reduced accuracy of the cardiac output measurements obtained using the impedance cardiography device.

A second disability associated with prior art impedance cardiography techniques relates to the detection of a degraded electrical connection or loss of electrical continuity between the terminals of the electrode and the electrical leads used to connect thereto. Specifically, as the subject moves or sweats during the measurement, the electrolyte of the electrode may lose contact with the skin, and/or the electrical leads may become partially or completely disconnected from the terminals of the electrode. These conditions result at best in a degraded signal, and at worst in a measurement which is not representative of the actual physiological condition of the subject.

Another significant consideration in the use of electrodes as part of impedance cardiographic measurements is the downward or normal pressure applied to the subject in applying the electrode to the skin, and connecting the electrical leads to the electrode. It is desirable to minimize the amount of pressure needed to securely affix the electrode to the subject's skin (as well as engage the electrical lead to the electrode), especially in subjects whose skin has been compromised by way of surgery or other injury, since significant pressure can result in pain, and reopening of wounds.

It is also noted that it is highly desirable to integrate cardiac output measurement capability into a compact, rugged, and efficient platform which is readily compatible with different hardware and software environments. The prior art approach of having a plurality of different, discrete stand-alone monitors which include, for example, a dedicated, redundant display and/or other output or storage device is not optimal, since there is often a need to conserve space at the subject's bedside or even in their home (e.g., in outpatient situations), as well as cost efficiency concerns. Furthermore, a plurality of discrete stand-alone monitors necessarily consume more electrical power (often each having their own separate power supplies), and require the subject or clinician to remain proficient with a plurality of different user interface protocols for the respective monitors. In many cases, the individual stand-alone monitors are also proprietary, such that there is limited if any interface between them for sharing data. For example, where two such monitors require a common parametric measurement (e.g., ECG waveform or blood pressure), one monitor frequently cannot transmit this data to the other monitor due to the lack of interface, thereby necessitating repeating the measurement.

Recognizing these deficiencies, more recent approaches have involved the use of modular devices, wherein for example a common monitor/display function is utilized for a variety of different functional modules. These modules are generally physically mounted in a rack or other such arrangement, with the common monitor/display unit also being mounted therein. A common power supply is also generally provided, thereby eliminating the redundancy and diversity previously described. However, heretofore, impedance cardiography (ICG) equipment has not been made in such modular fashion, nor otherwise compatible with other modular devices (such as blood pressure monitoring or ECG equipment), such that such other signals can be obtained directly or indirectly from these devices and utilized within the ICG apparatus. The quality or continuity of these signals, whether obtained directly from the subject being monitored or from other modules, has not been readily and reliably provided for either.

Typical patient monitors include modules for several physiologic measurements such as ECG, blood pressure, temperature, and arterial pulse oximetry. The addition of ICG provides the physician with additional useful clinical information about the patient.

Furthermore, prior art ICG devices (modular or otherwise) do not provide the facility for direct transmission of the data obtained from the subject, or other parameters generated by the ICG device after processing the input data, to a remote location for analysis or storage. Rather, the prior art approaches are localized to the bedside or monitoring location. This is a distinct disability with respect to the aforementioned outpatient applications, since the subject being monitored must either manually relay the information to the caregiver (such as by telephone, mail, or visit), or perform the analysis or interpretation themselves. Additionally, it is often desirable to perform more sophisticated (e.g. algorithmic) comparative or trend analysis of the subject's data, either with respect to prior data for that same subject, or data for other subjects. The lack of effective transmission modes in the prior art to some degree frustrates such analysis, since even if the subject has the facility to perform the analysis (e.g., PC or personal electronic device with the appropriate software), they will not necessarily be in possession of their own prior data, which may have accumulated via monitoring at a remote health care facility, or that for other similarly situated subjects.

Based on the foregoing, there is a need for an improved apparatus and method for measuring cardiac output in a living subject. Such improved apparatus and method ideally would allow the clinician to repeatedly and consistently place the electrodes at the optimal locations. Additionally, such an improved apparatus and method would also permit the detection of degraded electrical continuity between the electrode terminal and skin, or the electrode terminal and electrical leads of the measurement system, and be adapted to minimize the normal pressure on the subject's tissue when applying the electrodes and electrical leads. The apparatus would further be adapted to interface with other monitoring/display systems and parametric measurement modules that may be coincidently in use, and have connectivity beyond the immediate locale of the apparatus to permit the ready transfer of data to and from one or more remote locations or devices. Facility for selecting the highest quality input from a number of different sources would also ideally be provided.

SUMMARY OF THE INVENTION

The present invention satisfies the aforementioned needs by providing an improved method and apparatus for measuring the cardiac output of a living subject.

In a first aspect of the invention, an improved apparatus for measuring the cardiac output (CO) of a living subject is disclosed. In one exemplary embodiment, the living subject is a human being, and the apparatus comprises a system having a plurality of electrode pairs, a constant current source, a plurality of electrical leads connecting the constant current source with the plurality of electrode pairs, a differential amplifier for measuring the differential voltage at the electrodes, and circuitry for measuring ECG potentials from the electrode pairs. A predetermined distance is maintained between each of the individual electrodes in each electrode pair, thereby mitigating error sources relating to the relative placement of individual electrodes from the cardiac output measurement. Cardiac stroke volume is measured using the aforementioned apparatus by applying a constant current to the stimulation electrodes, measuring the resulting voltage differential at the measurement electrodes, and determining the stroke volume from the measured voltage and a predetermined relationship describing intra-thoracic impedance. The system also measures cardiac rate via the ECG potentials at the electrodes; cardiac output is then determined using the measured cardiac stroke volume and cardiac rate from the ECG potential.

In a second aspect of the invention, an improved cardiac output electrode assembly is disclosed. In one exemplary embodiment, the electrode assembly comprises a pair of electrode terminals disposed a predetermined distance from one another within an insulating substrate using a "snap" arrangement and electrolytic gel interposed between the electrode and skin of the subject. The substrate and gel materials of the electrode assembly are advantageously selected so as to provide a uniform and firm physical contact of the gel (and accordingly the electrode terminals) with the skin of the patient, and position of the terminals with relation to one another. The predetermined spacing of the electrodes also facilitates the detection of discontinuities in the system (such as an electrode becoming disconnected from the patient) through the measurement and comparison of impedance waveforms obtained from various electrode terminals. Additionally, the electrode pairs are used in conjunction with connectors having opposable jaws adapted such that no downward or normal pressure need be applied when a connector is fastened to an electrode terminal, yet consistent electrical properties are maintained.

In a third aspect of the invention, an improved method of measuring the cardiac output of a living subject is disclosed. The method generally comprises providing a plurality of electrode pairs; positioning the electrode pairs at predetermined locations above and below the thoracic cavity, generating a constant current; applying the constant current to one electrode of each of the electrode pairs; measuring the voltage at the second electrode of each electrode pair; determining cardiac stroke volume from the measured voltage; and determining cardiac output based on stroke volume and cardiac rate. In one exemplary embodiment, four electrode pairs are utilized, each having a predetermined spacing between both of the individual electrodes of the pair. The electrode pairs are placed at locations above and below the thoracic cavity of the subject, on both the right and left sides. Both differential voltage (related to the time-variant component of total thoracic impedance) and cardiac rate are measured via the electrode pairs for both sides of the subject.

In a fourth aspect of the invention, an improved method of monitoring the electrical continuity of a plurality of electrodes in an impedance cardiography system is disclosed. In one exemplary embodiment, the method comprises providing a plurality of electrically conductive terminals; disposing the terminals in relation to the thoracic cavity of a subject; generating a current between a first terminal and a second terminal, the current passing through at least a portion of the thoracic cavity; measuring an impedance waveform from the second terminal; and comparing the measured impedance waveform to a similar waveform measured from another terminal, the difference between the impedance waveforms being used to evaluate the electrical continuity of the first terminal.

In a fifth aspect of the invention, an improved impedance cardiography (ICG) module adapted to implement various of the foregoing aspects is disclosed. The module comprises a plurality of interfaces adapted to receive signals such as impedance and ECG waveforms; determinations of cardiac output (CO) and other related parameters are output via another interface to a host or monitoring device. In one exemplary embodiment, the module of the present invention comprises a digital processor-based device adapted to process impedance and other signals derived from one or more living subjects, and output signals to the monitor/display unit according to an established communications protocol. A microprocessor/DSP architecture is used in conjunction with signal filtration, analog-to-digital conversion, and other signal conditioning/processing within the module to extract useful cardiographic information from the patient signals received via the interfaces, and communicate this information to the monitor/display unit or other output device under control of the microprocessor. Other inputs such as the subject's blood pressure, multiple ECG waveforms, and the like may be utilized by the module during the aforementioned CO determination. The module may further be configured to generate the stimulation signal (e.g., constant current previously described) which is provided to the patient electrodes. In another embodiment, the module is further configured for impedance cardiographic (ICG) and electrocardiographic (ECG) waveform fiducial point detection and analysis using discrete wavelet transforms.

In yet another embodiment, the module includes a network interface adapted to couple the module to a data network capable of distributing the data generated by the module and other devices to local and/or remote network nodes, such as local stations within a health care facility, or to a remote health care or medical facility in the case of outpatient applications. Communication with other network nodes, locations, or personal electronic devices is accomplished using, for example, modulator/demodulator (modem) apparatus, wireless interface such as Bluetooth™, local- or wide-area network (LAN/WAN) topologies, circuit or packet-switched high-bandwidth data networks (such as asynchronous transfer mode), internet, intranet, the Wireless Medical Telemetry Service (WMTS) medical band (608–614 MHz), synchronous optical networks (SONET), FDDI, or even satellite communications.

In yet another embodiment, the ICG module of the invention comprises a yoke adapted to interface with a fixed or mobile electrocardiograph system. In one exemplary embodiment, the yoke is highly mobile and is adapted to electrically interface with the leads attached to the subject, as well as with the host monitor. The yoke further may include indications of the operating status of the yoke, as well as other data interfaces for transmitting ICG data to, and receiving other types of data (such as blood pressure data) from, other processing modules. In another embodiment, the yoke comprises a wireless data interface (such as Bluetooth™ or IEEE Std. 802.11 WLAN interface) between the yoke and the monitor. In yet another embodiment, the yoke is provided with a wireless interface between itself and the patient electrodes.

In yet another embodiment, the ICG module apparatus is configured to operate in conjunction with a dialysis (e.g., hemodialysis) system. Because cardiovascular events account for over 50% of deaths in dialysis patients per year in the United States, more vigilant cardiovascular disease management, including hemodynamic monitoring through impedance cardiography, may increase the survival rate of this patient population. The ICG module is adapted to receive data such as patient blood pressure from the dialyzer or one of the dialyzer's modules, which may operate contemporaneously with the ICG module while the patient is being dialyzed and monitored.

In yet another embodiment, the improved ICG module of the invention comprises a card or board level plug-in module adapted for receipt within a host device such as a personal computer or dedicated monitor/display unit.

In a sixth aspect of the invention, an improved method of waveform selection for input to the module processing is disclosed. In one exemplary embodiment, the input waveforms comprise ECG waveforms used in the CO determination, and the method comprises evaluating each waveform for signal quality based upon at least one parameter; ranking each waveform based on the foregoing quality evaluation; and selecting the one waveform with the best rank for further processing. The Q and R fiducial points are used to determine the quality evaluation parameters, which may include for example R-wave amplitude, QR interval difference, and RR interval difference. In this fashion, the module of the present invention evaluates the various sources of input data, and selects the best one from the available signals for further signal processing.

In a seventh aspect of the invention, an improved software environment adapted for use with the aforementioned ICG module is disclosed. In one exemplary embodiment, the software environment comprises initialization, operating, and processing modules adapted to perform various start-up, signal processing, communication, and error detection functions within the module.

BRIEF DESCRIPTION OF THE DRAWINGS

FIGS. 2a and 2b are perspective and cross-sectional views, respectively, of a prior art impedance cardiography electrode assembly.

FIGS. 15a–c are top, rear, and front plan views, respectively, of the module of FIGS. 12–14, configured so as to be received within an equipment rack.

DETAILED DESCRIPTION OF THE INVENTION

Figure 1:
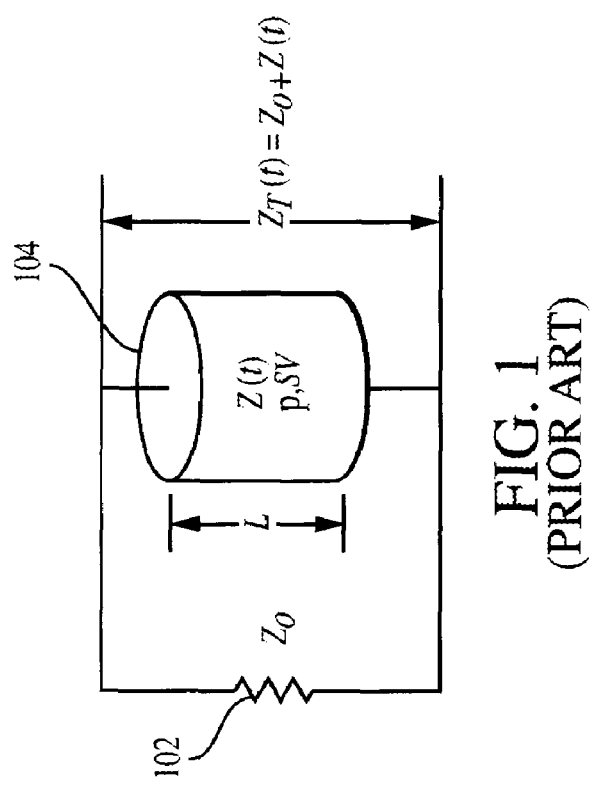
FIG. 1 is schematic diagram illustrating the parallel column model of the impedance of the thoracic cavity of a human being.

Reference is now made to the drawings wherein like numerals refer to like parts throughout.

It is noted that while the invention is described herein in terms of an apparatus and method for determining cardiac output suitable for use on the thorax of a human subject, the invention may also conceivably be embodied or adapted to monitor cardiac output at other locations on the human body, as well as monitoring cardiac output on other warm-blooded species. All such adaptations and alternate embodiments are considered to fall within the scope of the claims appended hereto.

As used herein, the term "digital processor" is meant generally to include all types of digital processing devices including, without limitation, digital signal processors (DSPs), reduced instruction set computers (RISC), general-purpose (CISC) processors, microprocessors, and application-specific integrated circuits (ASICs). Such digital processors may be contained on a single unitary IC die, or distributed across multiple components.

As used herein, the terms "monitor" and "monitoring device" are used generally to refer to devices adapted to perform monitoring, display, user interface, and/or control functions. Such devices may be dedicated to a particular function, or multi-purpose devices adaptable to performing a variety of functions and/or interfacing with a number of functional modules.

Methodology

Referring now to FIGS. 3a-5, the general methodology of measuring cardiac output in a living subject according to the invention is described.

As previously discussed, the thoracic impedance $Z_T(t)$ of a living subject may be modeled as comprising a constant impedance, $Z_o$, and time-varying impedance, $\Delta Z(t)$. According to the well-known "parallel-column" model of the thorax, this change in thoracic impedance, $\Delta Z(t)$, is related to the pulsatile blood volume change. In this model, illustrated in the form of a schematic diagram in FIG. 1 herein, effectively constant tissue impedances such as bone, muscle, and fat are modeled as a conducting volume $Z_o$ 102 in parallel with the pulsatile impedance of the blood $\Delta Z(t)$ 104. This second impedance 104 is a time-varying fluid column with resistivity, ρ, cylindrical length, L, and a time-varying cross-sectional area that oscillates between zero and a value A, the latter which correlates to the stroke volume V. When the pulsatile volume is at a minimum in the cardiac cycle, all the conducting tissues and fluids are represented by $Z_o$. During the cardiac cycle, the cylinder cross-sectional area increases from zero until the cylinder's volume equals the blood volume change.

Because $Z_o$ is much greater than $\Delta Z(t)$, the relationship of Eqn. (2) holds:

$$SV = \rho\left(\frac{L^2}{Z_0^2}\right)VET\frac{dZ(t)}{dt_{min}}, \quad (2)$$

where L is the distance between the measurement electrodes in cm (FIG. 3a), VET is the ventricular ejection time in seconds, and $$\frac{dZ(t)}{dt_{min}}$$

is the magnitude of the largest negative derivative of the impedance change occurring during systole in ohms/s. Often, the impedance derivative 400 is purposely inverted as shown in FIG. 4 so that the original negative minimum change will appear as a positive maximum 402, $$\frac{dZ(t)}{dt_{max}},$$

in a manner more familiar to clinicians.

Figure 3B:
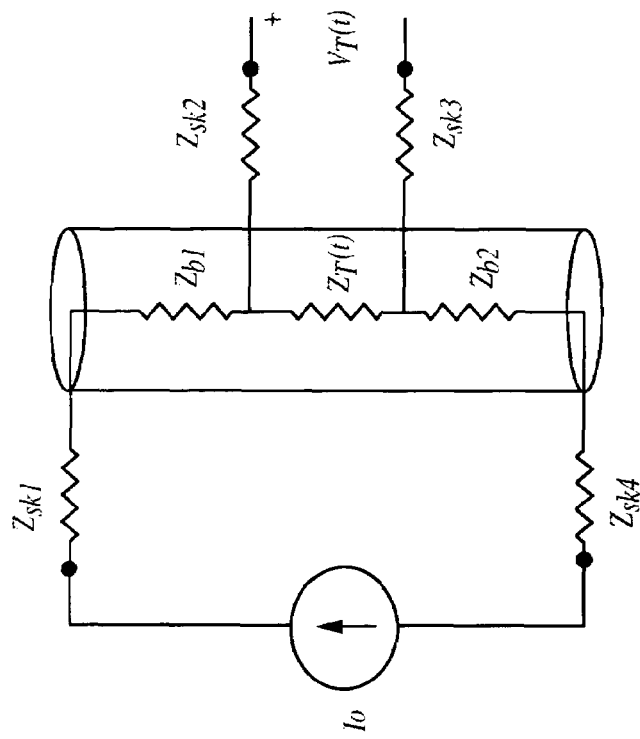
FIG. 3b is a schematic diagram illustrating the measurement of cardiac output using the electrode arrays and current source of the present invention.
Figure 3A:
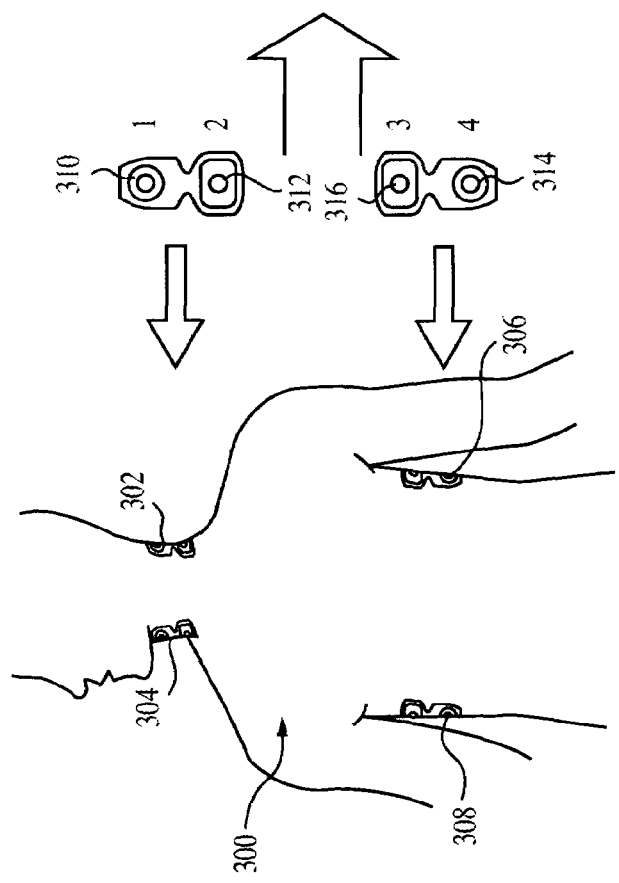
FIG. 3a is a plane view of a typical human thorax illustrating an exemplary placement of the electrode arrays of the present invention during cardiac output measurement.

The ventricular ejection time (VET) is estimated from features in the impedance waveform, which is obtained from the measurement terminals of the electrode arrays 302, 304, 306, 308 placed on various locations of the subject's thorax as illustrated in FIGS. 3a and 3b. In the present embodiment, a value of 150 ohm-cm is used for the resistivity of the blood, although it will be recognized that other values may be substituted as appropriate.

It is noted that the description of the volume of participating tissue may be modified. Rather than model the thorax as a cylinder as shown in FIG. 1 above, the thorax may instead be modeled as a truncated cone (as first described by Sramek and Bernstein). This approach results in a modified stroke volume calculation as in Eqn. (3):

$$SV = \frac{L^3}{4.25 Z_0}VET\frac{dZ(t)}{dt_{min}}. \quad (3)$$

With either of the two aforementioned approaches (i.e., cylindrical or truncated cone), the pulsatile impedance is estimated using Ohm's law, which is well known in the electrical arts. Specifically, current from a constant current source, $I_T(t)$, is applied, and the resulting voltage, $V_T(t)$, is measured in order to calculate the ratio of Eqn. (4):

$$Z_T(t) = \frac{V_T(t)}{I_T(t)}. \quad (4)$$

In the selected frequency range (i.e., 68 kHz), the typical impedance associated with a human subject's skin is 2 to 10 times the value of the underlying thoracic impedance $Z_T(t)$.

To aid in eliminating the contribution from skin and tissue impedance, the present invention uses at least two, and typically four electrode arrays 302, 304, 306, 308 for measurement, as shown in FIG. 3a. The physical construction and these electrode arrays is described in detail with reference to FIGS. 7a-8 herein.

In a simple application, one electrode array 302 comprising a stimulation electrode terminal 310 and a measurement electrode terminal 312 is applied above the thorax 300 of the subject, while a second electrode array 304 (having stimulation electrode terminal 314 and measurement electrode terminal 316) is applied below the thorax 300. The AC current from the current source is supplied to the stimulation electrode terminals 310, 314. As shown in FIG. 3b, current flows from each stimulation electrode terminal 310, 314 through each constant skin impedance, $Z_{sk1}$ or $Z_{sk4}$, each constant body tissue impedance, $Z_{b1}$ or $Z_{b1}$, and each constant skin impedance, $Z_{sk2}$ or $Z_{sk3}$, to each measurement electrode terminal 312, 316. The voltages at the measurement electrode terminals 312, 316 are measured and input to a differential amplifier to obtain the differential voltage, $V_T(t)$. The desired thoracic impedance, $Z_T(t)$, is then obtained using the relationship of Eqn. (4).

As shown in FIG. 3a, two sets of electrode arrays may advantageously be used to monitor the impedance associated with the left and right portion of the thorax 300 in the present invention. When eight electrode terminals (four arrays 302, 304, 306, 308) are used in this manner, the four measurement arrays are also used to obtain an electrocardiogram (ECG), based on one of four vectors modified from Lead I, II, III, or IV. The resulting electrocardiograms are based on the original Lead configurations, but are not of diagnostic quality. Regardless of the modified Lead configuration used, the Q wave of the ECG QRS interval is used to determine the heart rate and to trigger measurements of VET within the $$\frac{dZ(t)}{dt}$$

waveform.

Figure 5:
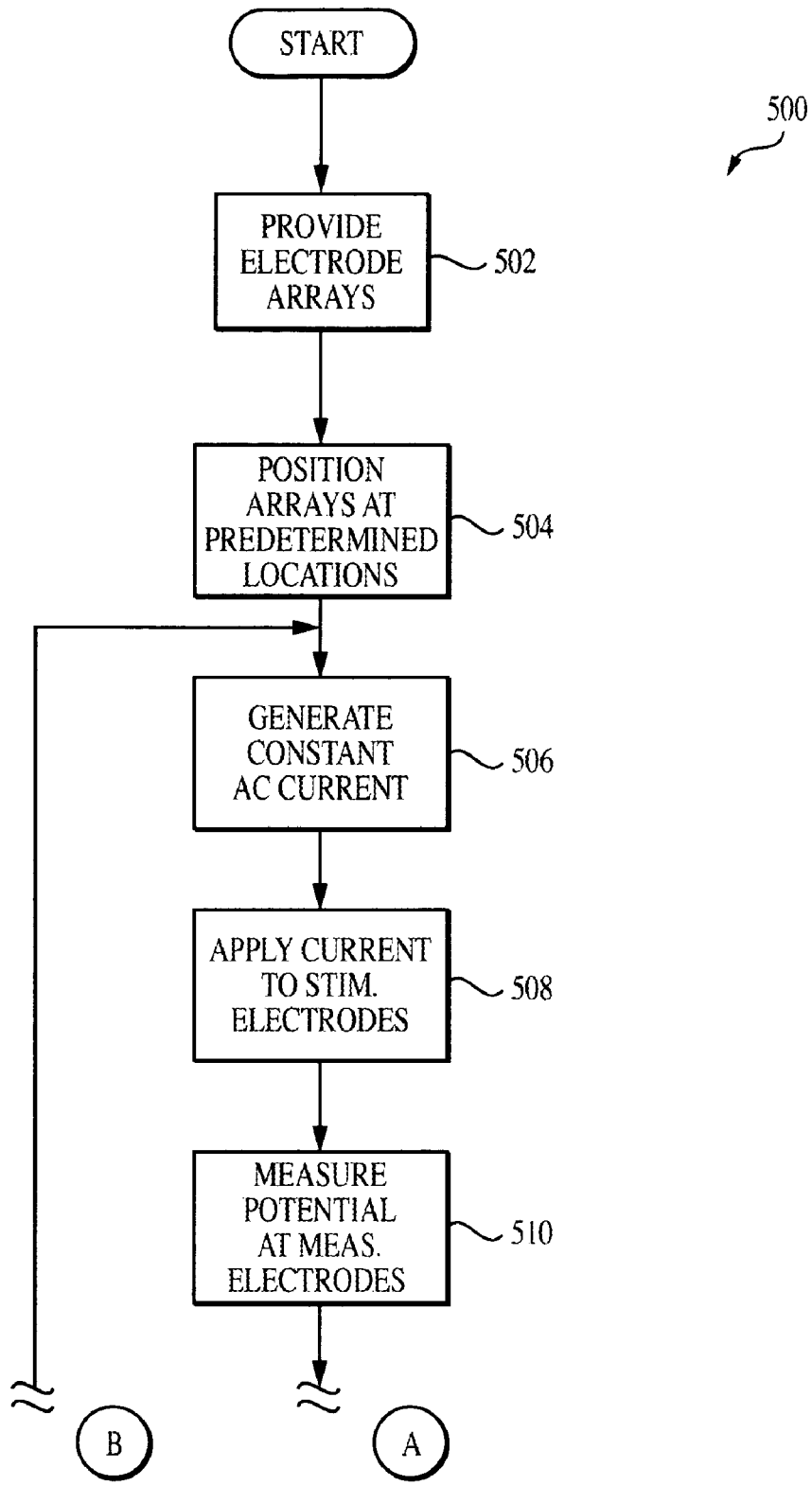
FIG. 5 is a logical flow diagram illustrating one exemplary embodiment of the method of measuring cardiac output within a living subject according to the invention.
Figure 5:
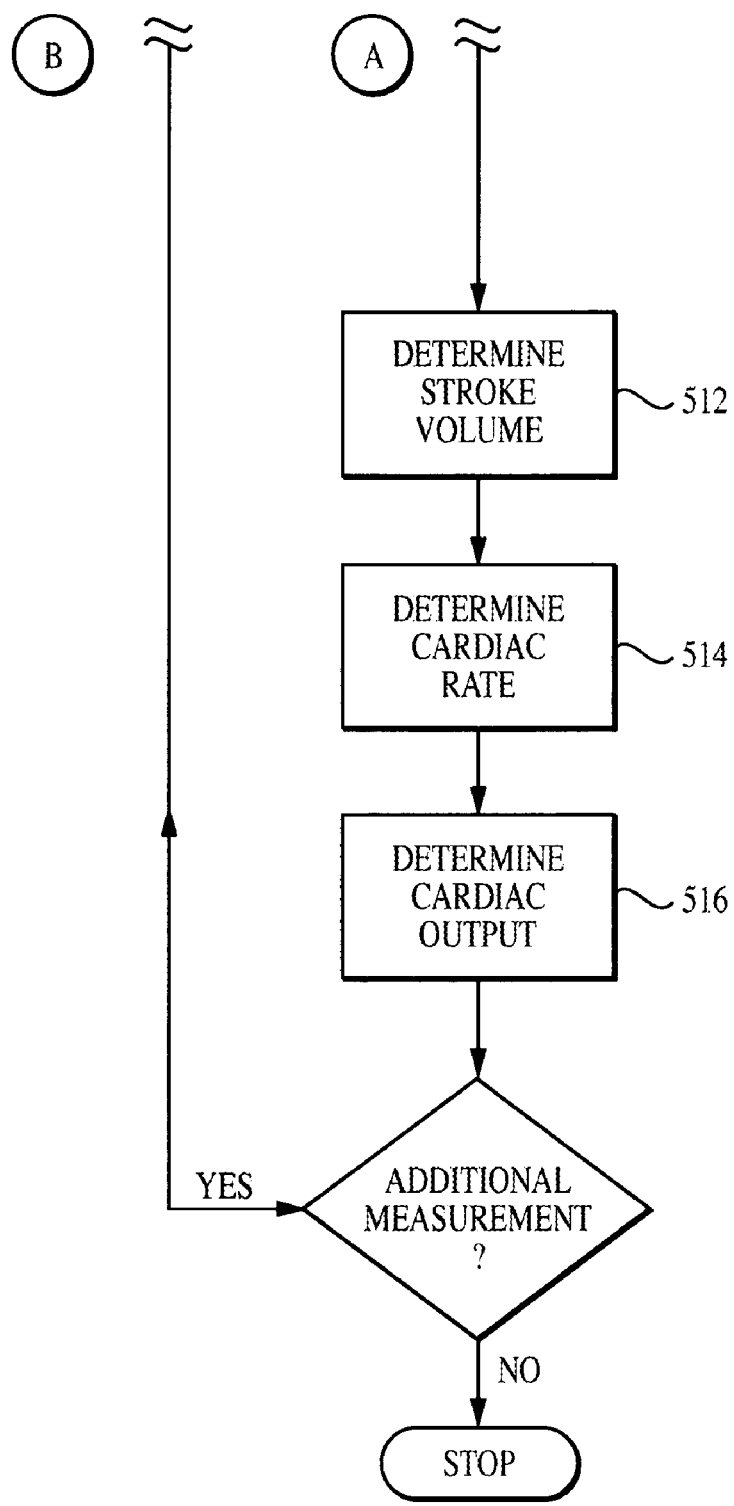

FIG. 5 illustrates the logical flow of the method of measuring cardiac output according to the invention. As shown in FIG. 5, the method 500 generally comprises first providing a plurality of electrode "arrays" of the type previously described herein per step 502. The electrode arrays are positioned at predetermined locations above and below the thoracic cavity per step 504, as illustrated in FIG. 3a herein. In one embodiment of the method, these locations are chosen to be on the right and left sides of the abdomen of the subject, and the right and left sides of the neck. These locations, with prior art band electrodes, were first used by Kubicek. Other locations and/or combinations of arrays may be substituted with equal success.

Next, a substantially constant AC current is generated in step 506, and the current applied to the stimulation electrode terminal 310, 314 of each of the electrode arrays in step 508. The voltage generated at the measurement electrode terminal 312, 316 of each electrode array is next measured in step 510. As previously discussed, this voltage is generally reduced from that applied to the stimulation electrode by virtue of the impedance of, inter alia, the thoracic cavity. Note that the measured voltage may be absolute, or relative (i.e., a differential voltage) as desired. Next, in step 512, the cardiac stroke volume from the measured voltage, using for example the relationship of Eqn. (3) above. Cardiac rate (step 514) is also determined by using the measurement electrodes to sense the ECG potentials generated by the heart of the subject. Lastly, in step 516, cardiac output is determined based on the stroke volume determined in step 512 and the cardiac rate in step 514 using the relationship of Eqn. 1 above.

Apparatus

Figure 6:
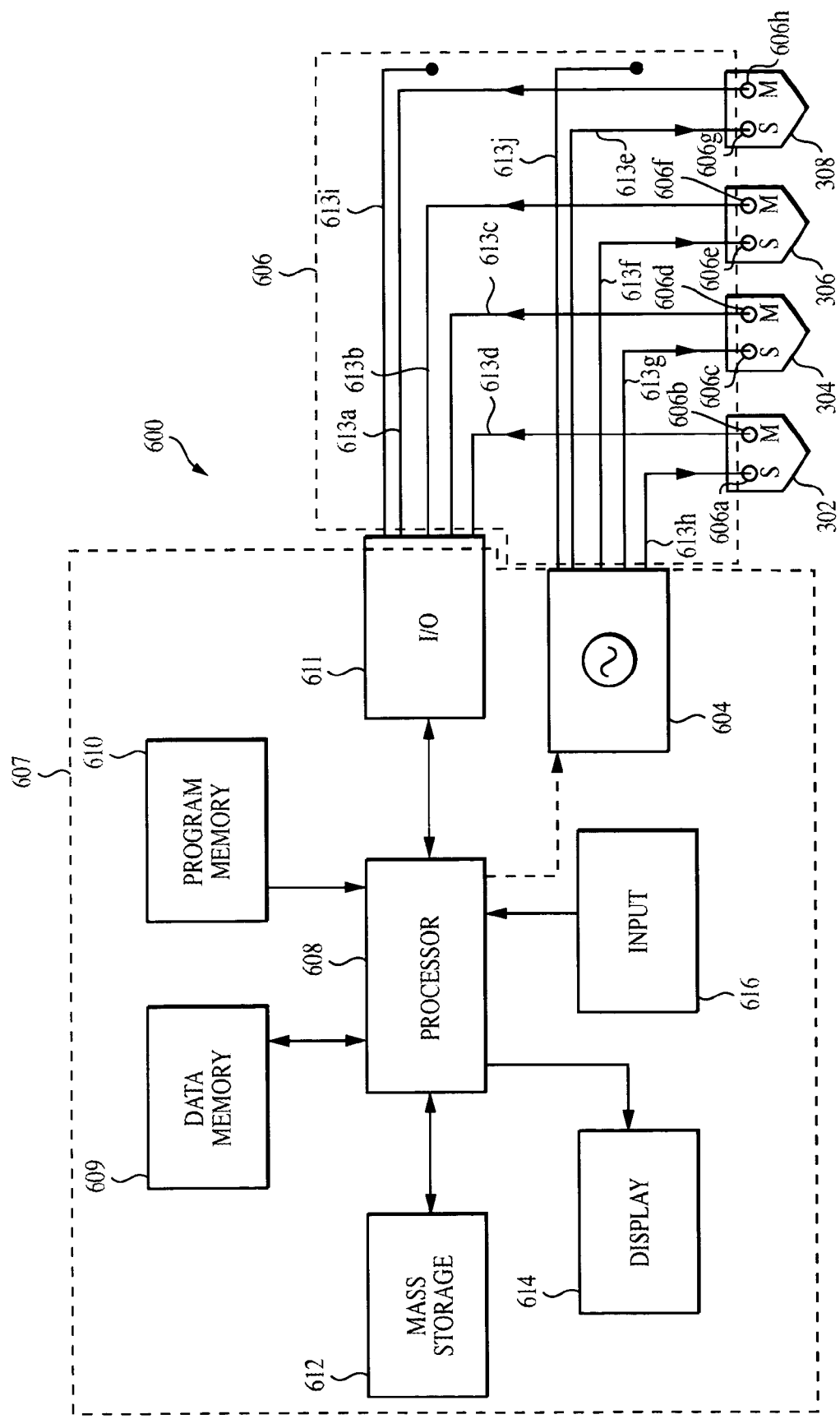
FIG. 6 is a logical block diagram illustrating one exemplary embodiment of the cardiac output measurement system of the present invention.

Referring now to FIG. 6, a first embodiment of the apparatus for measuring cardiac output using the above-described technique is disclosed. In addition to the four electrode arrays 302, 304, 306, 308 previously discussed, the system 600 generally comprises an alternating current (AC) current source 604 capable of generating a substantially constant current, a plurality of electrical leads in the form of a multi-ended lead assembly 606 for connecting the instrument monitor 607 to the individual terminals of the electrode arrays 302, 304, 306, 308, a processor 608 with associated algorithms capable of running thereon for performing analysis of the signals measured from the measurement terminals, data and program memory 609, 610 in data communication with the processor 608 for storing and retrieving program instructions and data; an I/O interface 611 (including analog-to-digital converter) for interfacing data between the measurement electrodes and the processor 608; a mass storage device 612 in data communication with the processor for storing and retrieving data; a display device 614 (with associated display driver, not shown) for providing an output display to the system operator, and an input device 616 for receiving input from the operator. It will be recognized that the processor 608, memory 609, 610, I/O interface 611, mass storage device 612, display device 614, and input device 616 (collectively comprising the instrument monitor 607) may be embodied in any variety of forms, such as a personal computer (PC), hand-held computer, or other computing device. The construction and operation of such devices is well known in the art, and accordingly is not described further herein.

The applied current derived from the current source 604 is a 70 kHz sine wave of approximately 2.5 mA peak-to-peak. The measured voltage associated with the aforementioned sine wave is on the order of 75 mV peak-to-peak. These values are chosen to advantageously minimize electric shock hazard, although it will be appreciated that other frequencies, currents, or voltages may be substituted. The construction and operation of AC current sources is well known in the electronic arts, and accordingly is not described further herein.

The electrode lead assembly 606 of the illustrated embodiment contains a ten wire assembly (two wires are left unused) that branches to eight individual connectors 606a–h.

The conductors 613a–j of the lead assembly are fashioned from electrically conductive material such as copper or aluminum, and are insulated using a polymer-based insulation having the desired dielectric strength as is well known in the electrical arts. The length of the conductors may also be controlled so as to match the impedance of each individual conductor to that of the others within the assembly 606.

Using one of four modified lead configurations, the body surface potential is measured between two measurement electrodes. This time-varying voltage reflects the electrical activity of the heart, and contains one QRS interval per cardiac cycle. The biopotential is analyzed to identify each QRS complex. The frequency of QRS complexes determines the heart rate. The Q wave within the QRS complex is then used to trigger identification of VET within the $$\frac{dZ(t)}{dt}$$

waveform, as the opening of the aortic valve (the beginning of VET) occurs after the appearance of the Q wave.

Additional embodiments of the cardiac output measurement apparatus of the invention are described subsequently herein with respect to FIGS. 11–22.

Figure 7A:
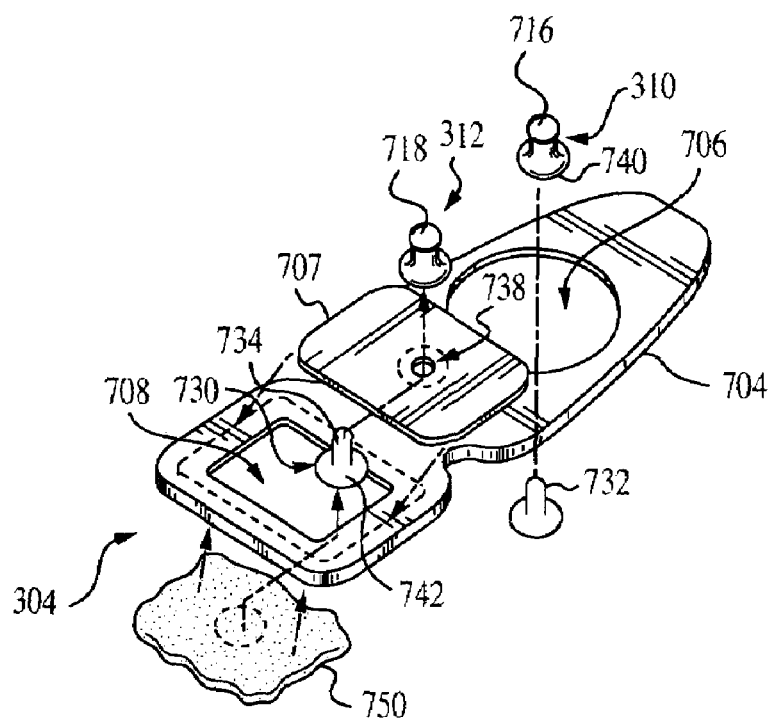
FIG. 7a is an assembly diagram illustrating the construction of a first embodiment of the electrode array of the present invention.
Figure 7B:
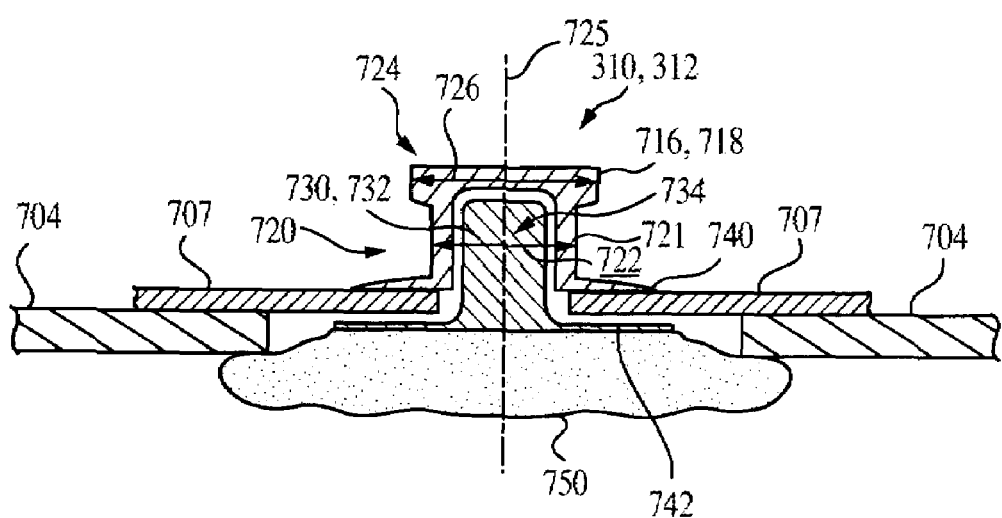
FIG. 7b is a cross-sectional view detailing the shape of the electrode terminals of the electrode array of FIG. 7a, and the construction thereof.
Figure 7D:
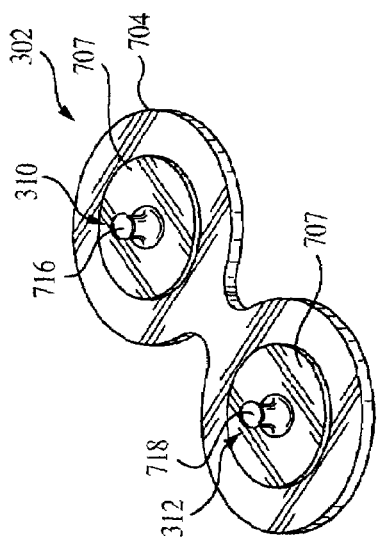
FIG. 7d is a perspective view of a second embodiment of the electrode array of the invention.
Figure 7C:
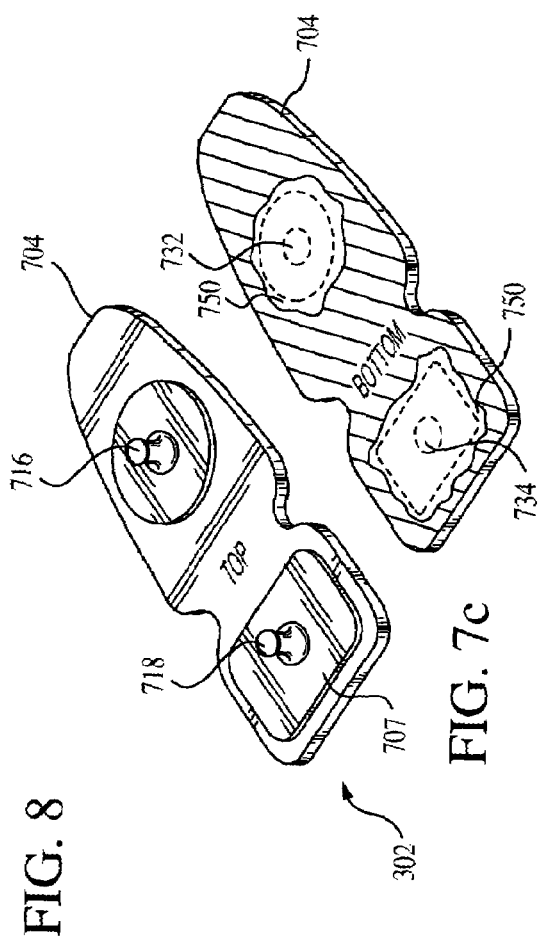
FIG. 7c illustrates top and bottom perspective views of the electrode array of FIG. 7a when fully assembled.

Referring now to FIGS. 7a–7c, the electrode arrays 302, 304, 306, 308 of the invention are described in detail. As illustrated in FIG. 7a, each array comprises a flexible substrate 704 having a plurality of apertures 706, 708 formed therein. In the illustrated embodiment, two terminals 310, 312 are disposed through the apertures such that the top portions 716, 718 of the terminals project above the plane of the substrate 704. The two terminals 310, 312 comprise a stimulation terminal 310 and measurement terminal 312 as previously described with respect to FIG. 3a. The stimulation terminal 310 is used to apply the potential necessary to generate the current flowing through the thoracic cavity of the subject. It will be noted that despite designation of one terminal as a "stimulation terminal" and one as a "measurement" terminal, the role of these terminals may be reversed if desired, since they are functionally and physically identical but for the potential applied thereto (or measured therefrom). It is noted that the asymmetric shape of the substrate 704 of the embodiment of FIGS. 7a–7c may be used to assist the clinician in rapidly determining which electrode is the stimulation electrode and which the measurement electrode, such as by assigning a convention that the end of the array having a given shape always contains the stimulation electrode. Additionally, the substrate may be shaped to adapt to certain physical features of the patient, such as by using a substrate having a broader width so as to better conform to the generally cylindrical shape of the subject's neck. Any number of different substrate shapes may be employed; FIG. 7d illustrates one such alternative shape.

As shown in FIGS. 7a–7c, the terminals 310, 312 are firmly held in place within the substrate 704 at a predetermined distance 705 by a mounting element 707 or any one of a variety of other constructions as will be described in greater detail below. The distance (measured centerline-to-centerline on the terminals 310, 312) is approximately 5 cm in the embodiment of FIG. 7a, although it will be recognized that other distances may be substituted. Desired distances may be determined through experimentation, anecdotal observations, calculations, or any other suitable method; however, experimental evidence obtained by the Applicant herein indicates that a distance of 5 cm is optimal for impedance cardiography measurements.

The substrate 704 in the embodiment of FIG. 7a is formed from a Polyethylene foam, although other materials such as cloth or vinyl may be substituted. The polyethylene foam is chosen for its compliance and flexibility, thereby allowing it to conform somewhat to the contours of the subject's anatomy, while still maintaining sufficient rigidity for maintaining the terminals 312, 314 in the desired position and orientation.

As shown in FIG. 7b, the terminals 310, 312 of each array comprise a generally cylindrical shaped sidewall portion 720 having a first diameter 722, and a top portion 724 having a second diameter 726, the second diameter 726 being greater than the first diameter 722 in order to assist in retaining a connector mated to the terminal 310, 312 as described in greater detail below. The outer wall 721 of the sidewall portion 720 is essentially vertical in orientation (i.e., parallel to the central axis 725 of the terminal 310, 312), while the top portion is progressively rounded as shown. The terminals may be manufactured from an extruded metal such nickel, with a coating of brass, or may be molded from carbon. Alternatively, the terminals may be molded of plastic, and coated with a metal such as gold or impregnated with carbon. The extruded metal possesses the advantage of low cost, while the molded plastic impregnated with carbon possesses the advantage of radiolucency. A terminal molded of plastic and coated with gold may possess low noise artifact.

The terminals 310, 312 of the electrode array comprise a two piece construction, having an upper terminal element 730 and a lower terminal element 732 as shown in FIGS. 7a and 7b. The post 734 of the lower terminal element 732 is adapted to be frictionally received within the cavity 736 of the upper terminal element when the two components are mated. In this fashion, the upper and lower elements 730, 732 form a single unit when assembled, with the mounting element 707 being frictionally held or "pinched" between the lower surface 740 of the upper element 730 and the upper surface 742 of the lower element 732. The post 734 of the lower element perforates the mounting element 707, or alternatively penetrates through a pre-existing aperture 738 formed therein. The lower elements 730, 732 of the electrode array terminals 310, 312 are coated with Ag/AgCl, although other materials with the desirable mechanical and electrochemical properties such as Zinc Chloride may be used if desired.

The electrolytic element 750 of each electrode array comprises an electrolytic gel of the type well known in the bio-electrical arts; in the present embodiment, the gel comprises an ultraviolet (UV) cured potassium chloride (KCl) gel, although it will be recognized that other types of compounds or materials may be used. UV curing of the gel allows the element 750 to have a more solidified consistency and improved mechanical properties, thereby preventing excessive spreading or thinning of the element when the array is applied to the subject while still maintaining its overall adhesiveness and electrolytic properties. As shown in FIGS. 7b and 7c, the element 750 is sized so as to encompass the edges 752 of the respective aperture 706, 708 in the substrate 704 over which it is placed when assembled, although other configurations may be used. The top portion 755 of the element 750 fits at least partially within the aperture 706, 708 and conforms substantially thereto, thereby effecting contact with the bottom surface 760 of the bottom terminal element 732. In this way, ions are passed between the skin of the subject and the terminals of the array via the gel element 750. The gel also provides for adhesion of the array to the skin of the subject, although the array of the present embodiment also includes a separate adhesive 762 which is applied to the bottom surface of the substrate 704, as shown in FIG. 7c.

Since the placement of the electrolytic element 750 with respect to the terminals 310, 312 of the array may in certain cases affect the ultimate measurements of cardiac output obtained with the system, the gel of the element 750 is advantageously placed in the embodiment of FIGS. 7a–c so as to be symmetric with respect to the terminal 310, 312. It will be recognized, however, that the element(s) 750 may also be placed so as to produce certain desired electrolytic conditions. Similarly, the element 750 may be split into two or more component parts if desired.

Figure 8:
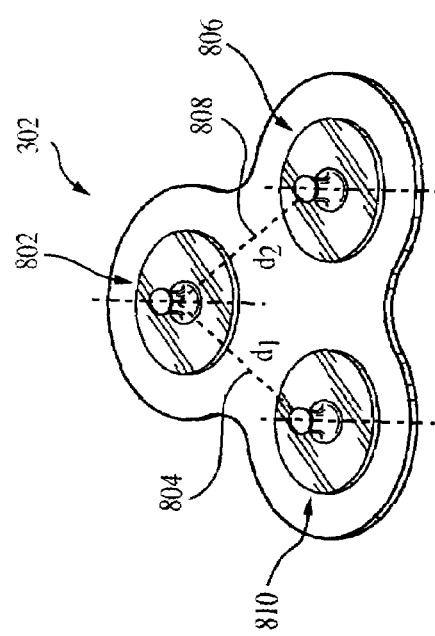
FIG. 8 is a perspective view of a third embodiment of the electrode array of the invention.

Furthermore, it is noted that while the embodiment of FIGS. 7a–c employs two fixed terminals that are effectively immovable within the substrate, means for allowing adjustment or change of the relative position of the terminals may be substituted. For example, as illustrated in FIG. 8, a terminal array having three terminal posts may be used, the second post 802 being spaced a first distance 804 from the first post 806, and the third post 810 being spaced a second distance 808 from the first post 806, such that the clinician can select one of two terminal spacings as desired.

Figure 9:
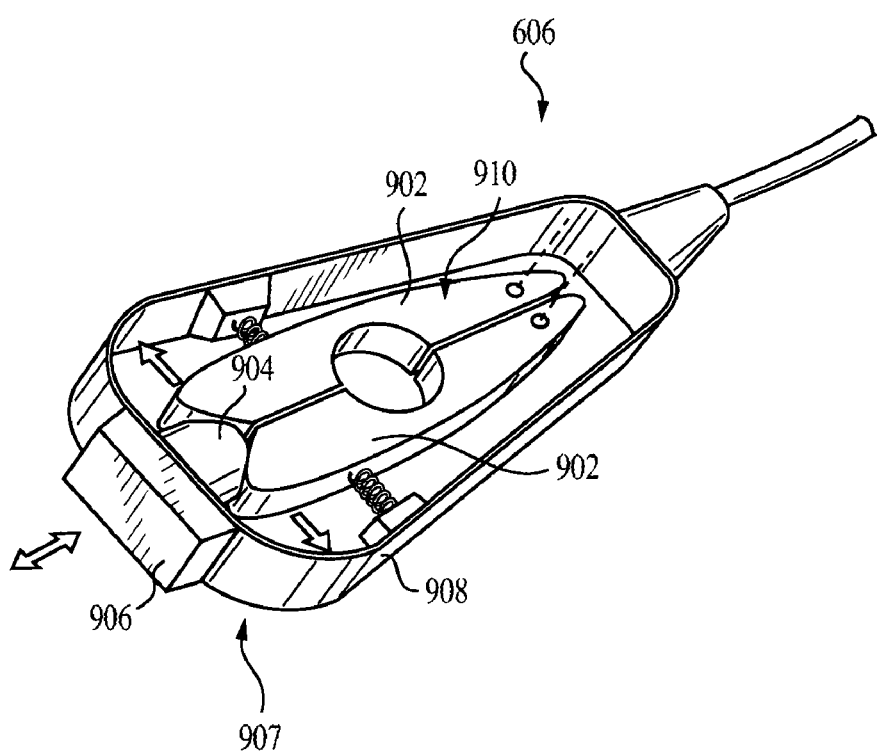
FIG. 9 is perspective view of one embodiment of a biased-jaw electrical connector as used in conjunction with the present invention.

As illustrated in FIG. 9, each electrode lead assembly connector 606a–h is designed to mitigate the downward force required to mate the connector with its respective electrode array terminal. Specifically, each connector 606a–h contains two spring-biased conductive jaws 902 that are spread apart by the cam surface 904 of an actuator button 906 disposed on the front 907 of the connector body 908. The connector jaws 902 and bias mechanism are designed to allow the upper and sidewall portions 724, 720 of the electrode terminal 310, 312 (FIG. 7b) to be received within the recess 910 of the jaws 902 when the button 906 is fully depressed. In this fashion, effectively no downward force is required to engage the connector to its respective terminal. The jaws 902 are contoured to engage substantially the entire surface of the sidewall portion 720 of the terminal when the actuator button 906 is released. Since the sidewall portion 720 of the terminal is effectively circular in cross-section, the connector may advantageously rotate around the axis of the terminal 310, 312 when lateral tension is applied to the conductor attached to that connector. U.S. Pat. No. 5,895,298 issued Apr. 20, 1999, entitled "DC Biopotential Electrode Connector and Connector Condition Sensor," and incorporated herein by reference in its entirety, describes a bias jaw electrical connector of the type referenced above in greater detail.

When used with the four two-terminal electrode arrays 302, 304, 306, 308 shown in FIG. 3a, each connector 606a–h is fastened to one of the two terminals 310, 312 of an electrode array. The 68 kHz constant current is applied from the current source to four electrode terminals (i.e., one terminal per array). Hence, complete circuits are formed between the current source and the I/O device 611 of the system 600 via the electrical conductors and connectors associated with the stimulation electrode terminals, the stimulation electrode terminals themselves, the thorax of the subject, the measurement terminals, and the electrical conductors and connectors associated with the measurement terminals.

Method of Evaluating Electrical Continuity

Figure 10:
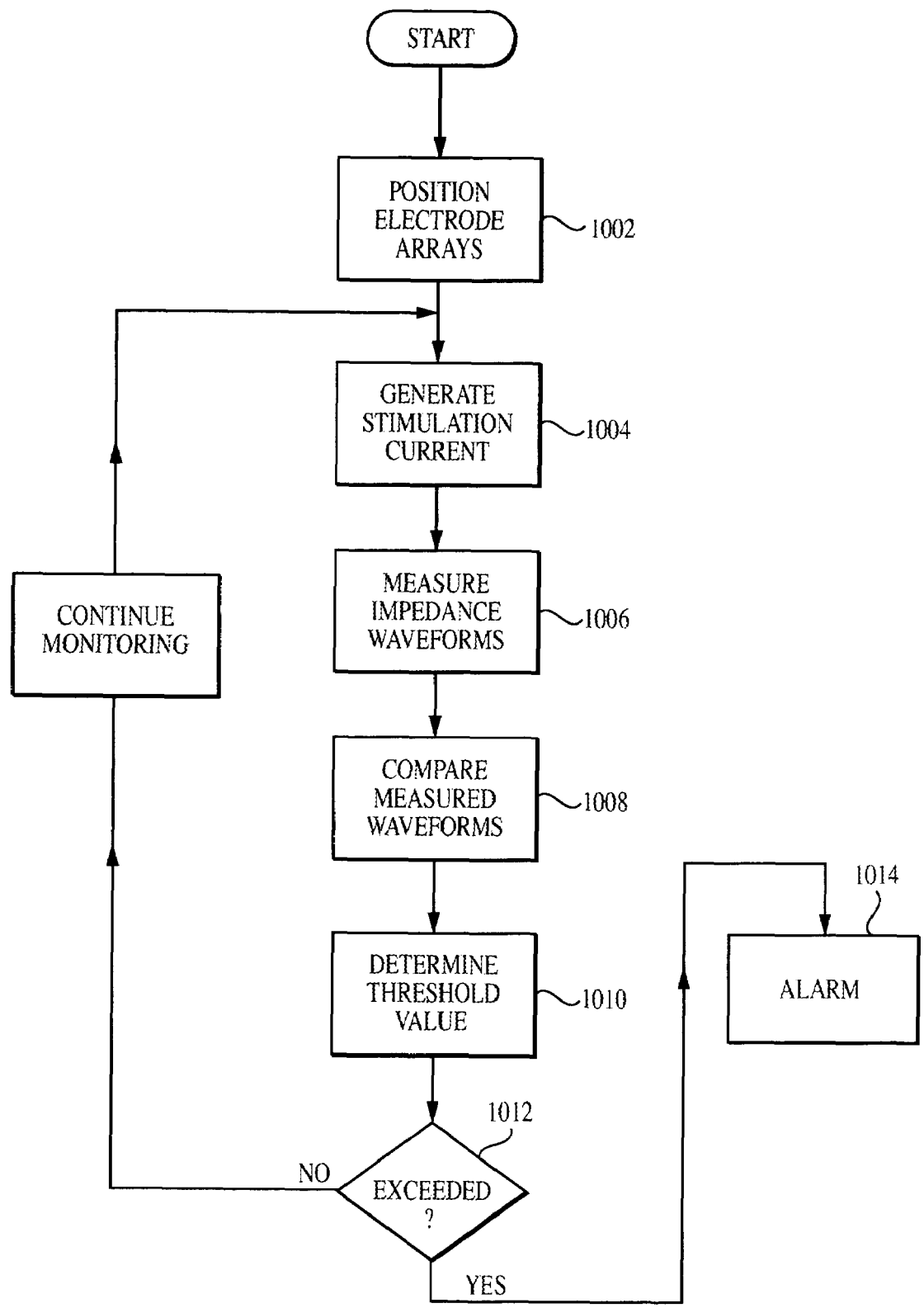
FIG. 10 is a logical flow diagram illustrating one exemplary embodiment of the method of evaluating electrical lead continuity according to the invention.

Referring now to FIG. 10, the method of evaluating the electrical continuity of one or more leads within the system is described. Note that while the following description is based on the two-terminal array configuration (FIGS. 7a–7c) and the use of four arrays as shown in FIG. 3a, the method may be applied to many alternate configurations with equal success.

First, in step 1002, the electrode arrays are disposed on the skin of the subject. The position at which the electrode arrays are disposed on the subject are measured in relation to the thoracic cavity as illustrated in FIG. 3a, or alternatively may be inferred by the weight and height of the subject. Next, a current is generated between the stimulation electrodes and the measurement electrodes of the respective arrays in step 1004. As previously discussed, the current passes through at least a portion of the subject's thoracic cavity, encountering a time-variant impedance therein.

An impedance waveform is then measured from two or more of the measurement terminals of the arrays in step 1006. The waveforms comprise measurements of impedance as a function of time, which is well known in the cardiographic arts. These measured waveforms are then compared to one another in step 1008 to detect changes or variations between them. In the present embodiment, two waveforms are differenced by way of a simple differencing algorithm resident on the processor 608 of the system 600 (FIG. 6), although it will be recognized that other approaches may be used. For example, the base impedance may be calculated for the left and right sides. The larger base impedance may then be subtracted from the smaller base impedance, with this difference then divided by the smaller impedance. The resulting percentage ratio, when greater than a predetermined threshold value, may represent the presence of detached or loose electrodes. While some variation between the waveforms is normal, significant variations are indicative of either a degraded electrical connection, such as between the electrode array terminal and its respective connector, or between the electrolytic gel and the skin of the patient, or even the gel and the terminal of the array or between the cable and connector. A threshold value is determined and set by the operator of the system in step 1010 such that when the threshold "difference" is exceeded as determined by the aforementioned algorithm (step 1012), the operator will be alerted to the degraded condition such as by a visual or audible alarm in step 1014.

In another embodiment of the method, the difference in impedance (or voltage) between the individual terminals 310, 312 of one or more electrode arrays is measured and used as the basis for the continuity determination. Specifically, the difference in the values measured from one terminal 310 with respect to another terminal 312 of the exemplary two-terminal array 302 illustrated herein is measured; when this value exceeds a certain threshold difference value (e.g., 650 Ohms, although other values may be substituted based on any number of factors), a loose electrode or otherwise degraded connection is suspected. It will be recognized that this methodology may also be employed when more that two electrical terminals are electrically connected to the system. For example, if three electrodes (e.g., electrodes 1, 2, and 3) of an electrode array are being used, the algorithm of the present invention would be adapted to measure the difference between each of the non-repeating permutations (i.e., 1–2, 1–3, and 2–3) and compare such differences to the threshold.

It will be recognized by those of ordinary skill that other approaches may be utilized for analyzing the impedance (voltage) measurements obtained from the electrode arrays in evaluating electrical continuity. Furthermore, it will be recognized that the aforementioned threshold value may be algorithmically determined and/or parametrically variant. For example, based on data obtained by the system before and/or during operation, the present invention may periodically or continuously calculate new threshold values as a function of time. Alternatively, the system may be adapted to calculate a plurality of such impedance difference values across each of the terminal arrays in use, and average the values periodically to maintain a "moving average" of impedance differences. As yet another alternative, other physiological parameters of the subject being monitored could be used as "triggers" for revised threshold determination and/or impedance difference calculation. Many other such variations and alternatives are possible consistent with the methodology of the present invention.

It is noted that the use of the multi-terminal electrode arrays having predetermined and substantially equal terminal spacing as previously described allows such comparisons between electrode waveforms to be made; errors resulting from uncontrolled spacing of the terminals are effectively eliminated. Using prior art electrodes, the aforementioned method would be largely ineffective, since these error sources would force the threshold value to be set artificially high, thereby potentially masking conditions of degraded electrical continuity which could affect the ultimate accuracy of and cardiac output estimation made by the system.

ICG Module

Referring now to FIGS. 11–14, the improved impedance cardiography module of the present invention is described. The ICG module of the invention utilizes the electrical bio-impedance measurements previously described herein to continuously generate a signal indicative of pulsatile thoracic impedance changes. This pulsatile thoracic impedance signal is processed to produce signals indicative of other related parameters, such as the ventricular ejection time (VET) and the maximum rate of change of pulsatile thoracic impedance, which are used to calculate the volume of blood pumped per stroke according to equations previously discussed. While described specifically in terms of the BioZ® ICG module manufactured by the Assignee hereof, it will be appreciated that the broader inventive concepts disclosed herein may be embodied in any number of different forms and combinations of functionality, several of which are described subsequently herein as alternate embodiments.

As previously discussed, the voltage developed across the thoracic impedance at any instant in time can vary due to a number of different factors. Specifically, the voltage is affected by four primary components: (i) base impedance; (ii) respiration; (iii) cardiac changes; and (iv) patient motion.

The base impedance comprises the largest component of the modulated waveform, and represents the nominal conductivity of the thorax. It is a function of the tissue and fluid distribution within the interrogated area. The average value of the base impedance, or TFI, is roughly 30 Ohms, but can vary from 5 to 60 Ohms in adult humans.

Inhalation and expiration by the patient causes significant impedance changes as gases enter and exit the lungs. The ventilation cycle is relatively long, typically 0.2 to 0.7 Hz with variable magnitude.

Impedance changes occur due to the cardiac cycle, such as after ventricular depolarization (QRS complex), and have very small magnitudes (approximately 0.05–0.3 Ohms). These impedance changes are the result of aortic expansion after blood is ejected from the ventricle, and contraction as blood is flows into the circulatory system.

Movement by the patient causes significant impedance changes due to fluid shifts and density/volume changes in the thorax, with varying frequency and magnitude. The motion component of impedance is effectively eliminated when the patient is monitored at rest.

Figure 11:
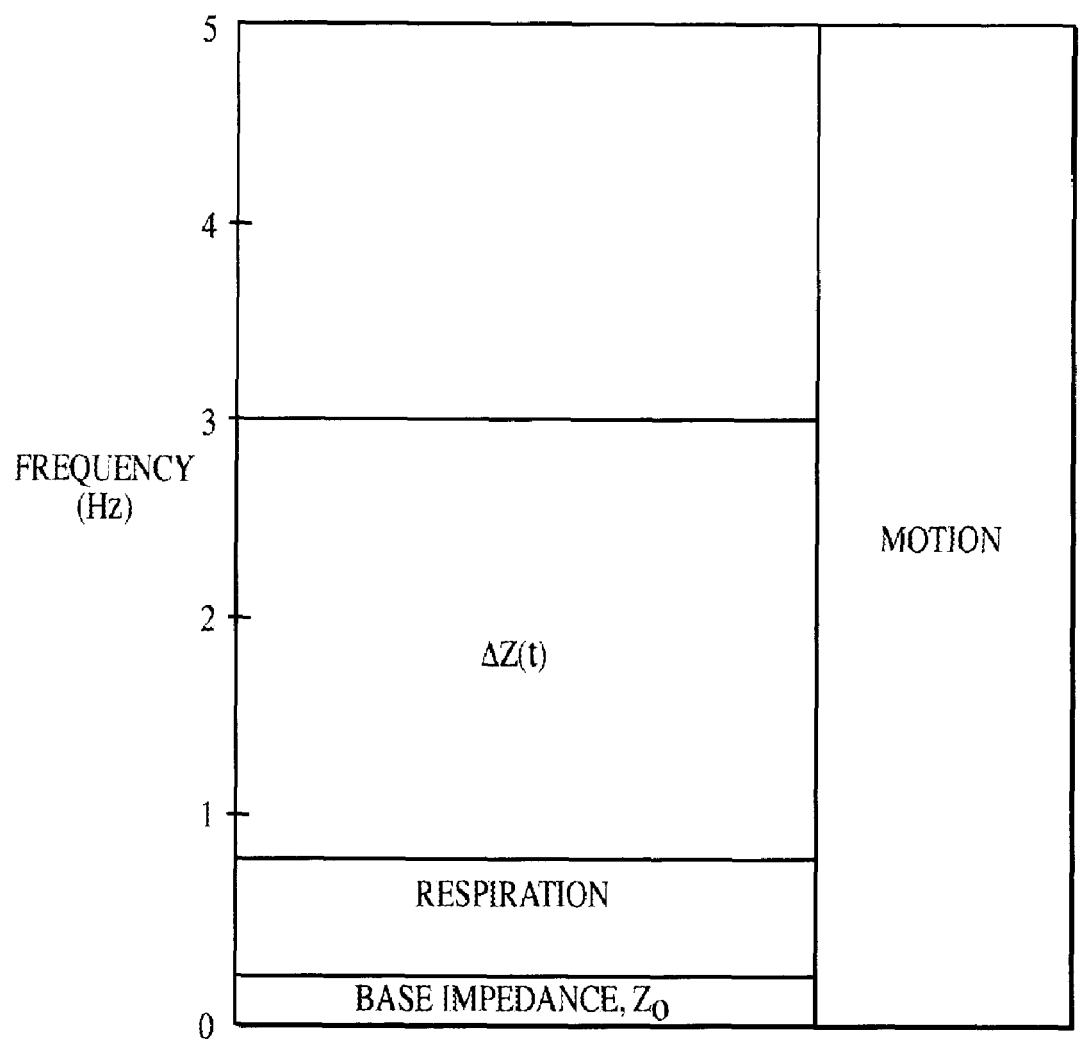
FIG. 11 is a graph illustrating the frequency ranges of thoracic signals for a typical adult human subject.

FIG. 11 is a graph illustrating the frequency ranges of these four signal components for a typical adult human subject.

The ICG module of the invention advantageously addresses the foregoing components of thoracic impedance through its signal processing circuitry and algorithms, now described in detail.

Figure 12:
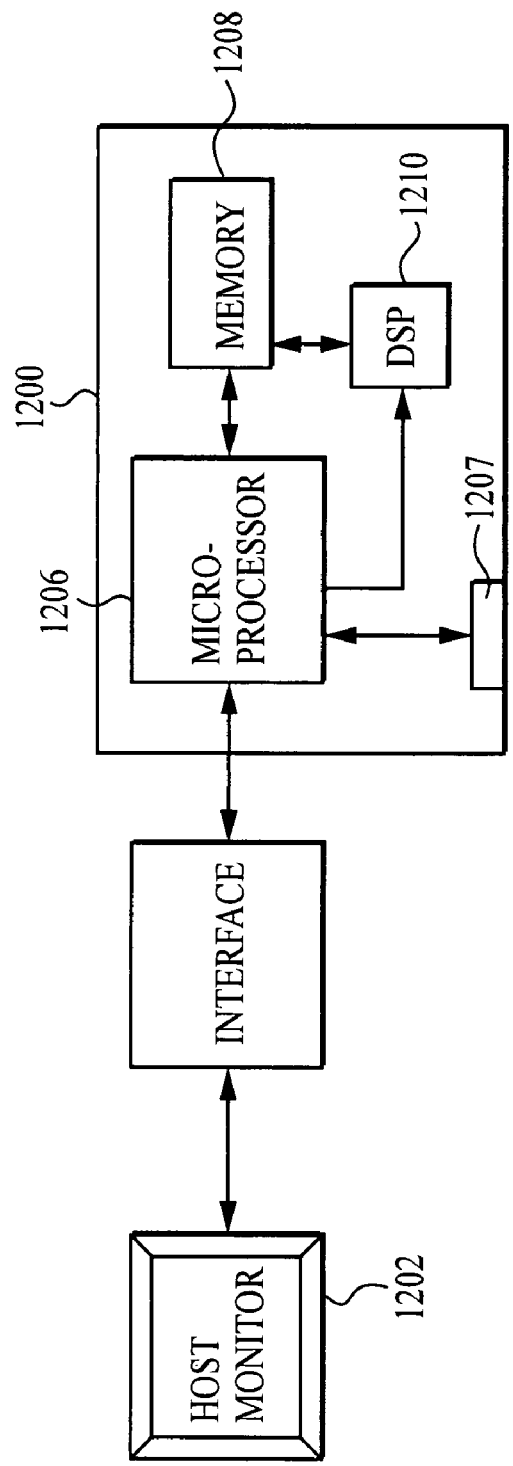
FIG. 12 is a functional block diagram illustrating one exemplary embodiment of the ICG module of the invention, including the connection of the module to a communications interface/monitoring system.

As shown in FIG. 12, the ICG module 1200 of the invention is electrically coupled to the host monitor 1202 via the interface device 1204. The ICG module 1200 generally comprises a microprocessor 1206, storage device 1208, and digital signal processor 1210, as described in greater detail below with respect to FIG. 13. The module 1200 communicates with a host monitor 1202 to continuously monitor and display the cardiac output and pulse rate of the subject under evaluation. Communications are in the illustrated embodiment conducted according to a predetermined protocol (such as a serial interface protocol of the type well known in the art), although other approaches may be substituted with equal success. The module further includes other features such as input power conditioning and "soft-start" current limiting functionality, software/firmware download from the host device, and electrical isolation (e.g., 4000 V) for the subject being monitored.

Figures 2, 13:
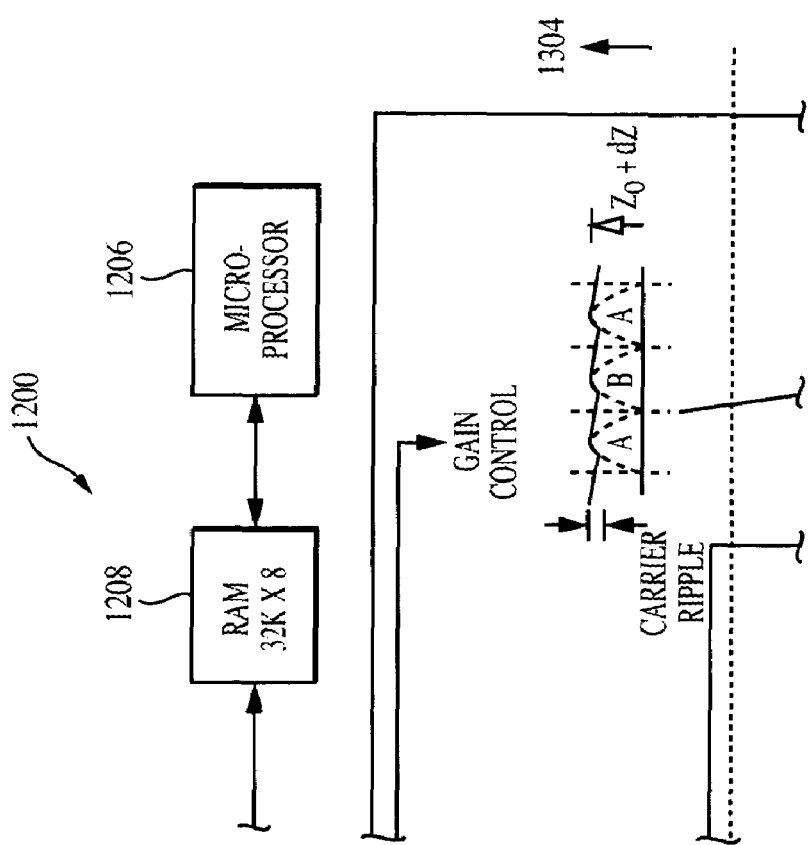
FIG. 13 is a functional block diagram illustrating the processor and patient interface boards of the ICG module of FIG. 12, and relationship of components comprising these boards.
Figures 3, 13:
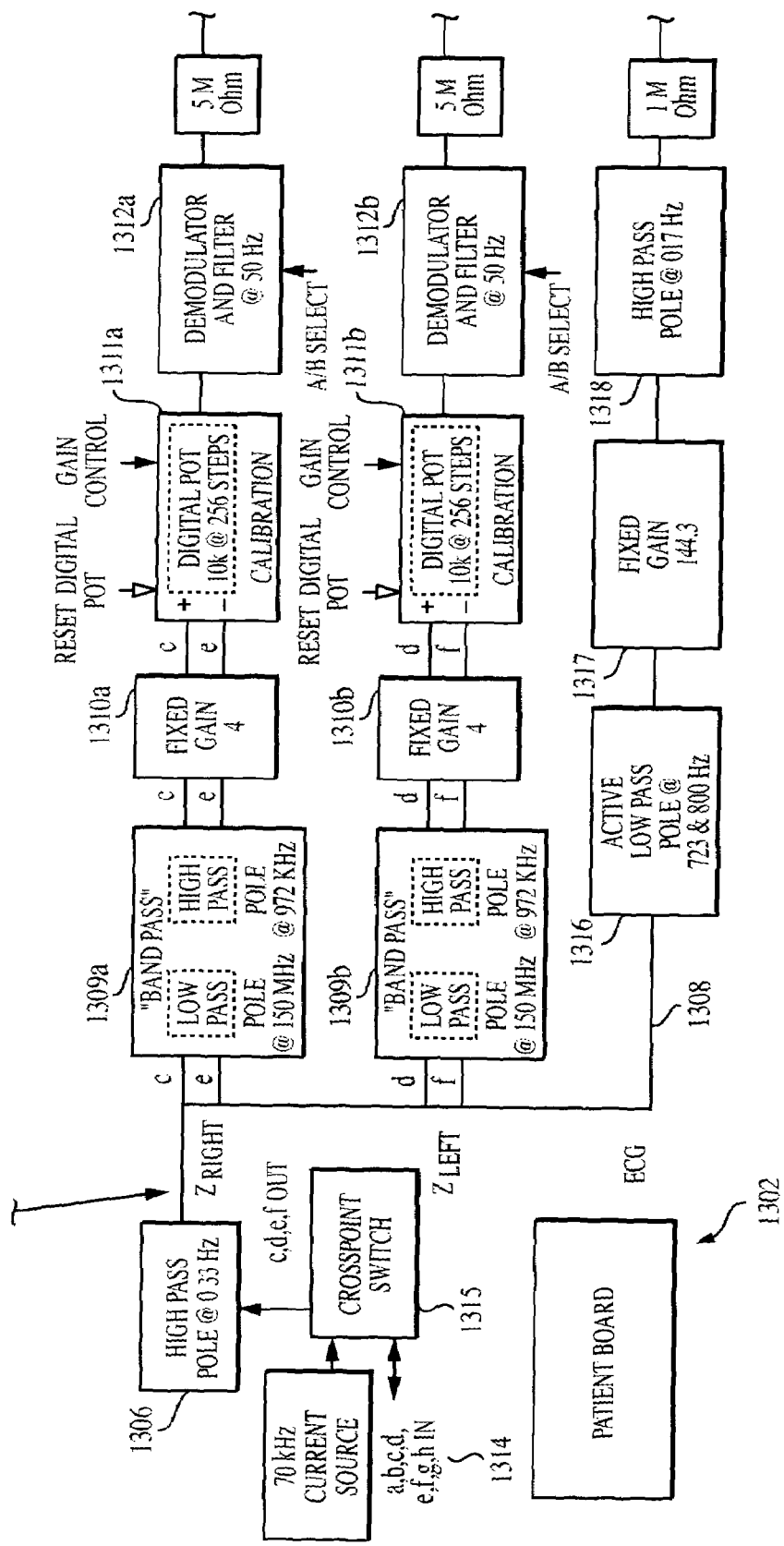
Figures 4, 13:
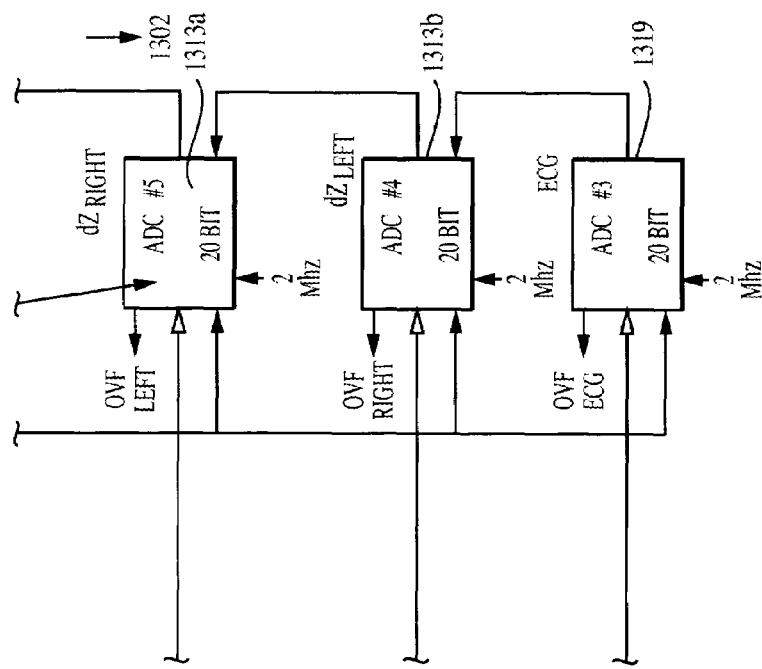
FIG. 4 is graph of the derivative of the time-variant component $\Delta Z(t)$ of thoracic impedance as a function of time, illustrating the systole "peak" used in determining ventricular ejection time (VET).

As shown in FIG. 13, the exemplary embodiment of the module 1200 comprises two component boards 1302, 1304, identified herein as the "patient board" 1302 and the "processor board" 1304. It will be recognized that these may or may not be separate physical boards or substrates. The patient board 1302 provides a number of functions, including (i) interface with the external signal sources; e.g., the patient leads and electrodes which provide, inter alia, the impedance and ECG waveform signals to the module; (ii) ECG vector select (described in greater detail below); and (iii) input signal filtration, conditioning, and domain conversion. The patient board 1302 also isolates the electrical (ECG) the mechanical ($\Delta Z$) components of cardiac activity from each other, and from the components of respiration and motion present in the signals derived from the subject under evaluation. A first high-pass filter (pole at 0.33 Hz) 1306 filters the input impedance waveform 1307 and ECG waveform 1308. Band-pass filters 1309a, 1309b comprising a low-pass filter with pole at 1.59 MHz and high-pass filter with pole at 9.72 kHz are used to further filter the respective high-pass filtered impedance waveforms of each input channel (a channel being defined for the purposes of this exemplary discussion as a pair of electrodes; i.e., "left" channel and "right" channel). Fixed gain amplifiers 1310a, 1310b receive the output of the band-pass filters 1309a, 1309b for each channel, and provide a fixed gain output signal to respective digital potentiometers 1311a, 1311b, the output of which is supplied to respective demodulators/filters 1312a, 1312b. The output of the demodulator/filter units 1312a, 1312b is passed through 5 M Ohm resistors and subsequently input to respective analog-to-digital converters (ADCs) 1313a, 1313b, which are clocked according to a 2 MHz clock signal (described below).

Figure 21:
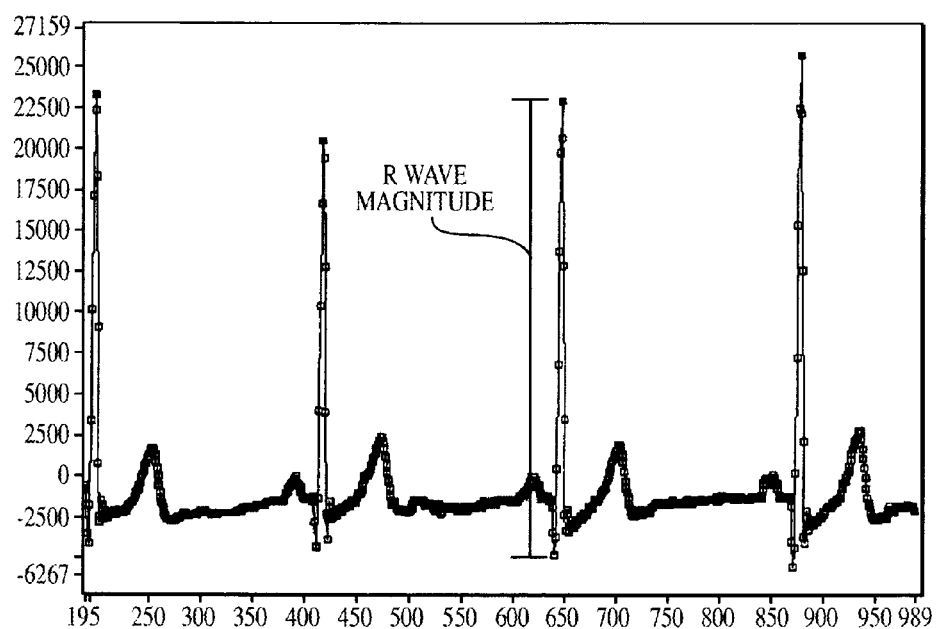
FIG. 21 is a graphical representation of the R-wave amplitude calculation according to the invention.
Figure 22:
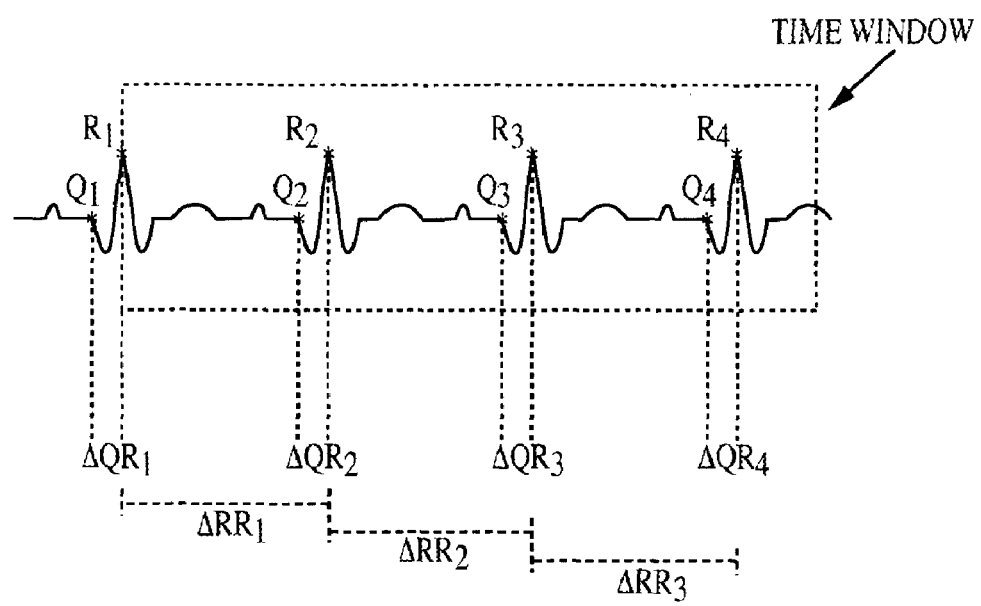
FIG. 22 is a graphical representation of the methodology for calculating the exemplary QR and RR interval difference parameters according to the invention.

The patient board 1302 further comprises a plurality of ECG inputs 1314 which are obtained from the aforementioned electrode pairs and input to a crosspoint switch 1315 (e.g., a 16×16 analog multiplexer such as the AD75019 device manufactured by Analog Devices), which selects the best "quality" input from among the four inputs as described in detail below with respect to FIGS. 20–22. The selected ECG signal is low-pass filtered 1316, amplified to a fixed gain 1317, high-pass filtered 1318, and then supplied (via 1 M Ohm resistor) to the ECG ADC 1319. The three ADCs 1313a, 1313b, 1319 output digitized signals to the DSP 1210 on the processor board 1304, described below.

The patient board 1302 also uses this crosspoint switch to provide several other functions, including connection of leads to the patient, provision of multiple ECG vectors, loose electrode testing (previously described), cable identification, and calibration.

The processor board 1304 comprises a digital signal processor (DSP) 1210 with direct memory access (DMA) of the type well known in the electronic arts, a microprocessor 1206, a storage device 1208 coupled with the DSP 1210 and microprocessor 1206 via a data bus, a first signal (constant current) source 1330 generating a nominal 70 kHz output signal, a second signal source 1332 generating a nominal 2 MHz output signal, a clock signal generator (12 MHz nominal), and digital-to-analog converter (DAC) 1334.

In one variant, the module is configured with a DC/DC converter operating at 90 kHz, and the aforementioned ICG current source at 70+/–6 kHz.

Figure 13A:
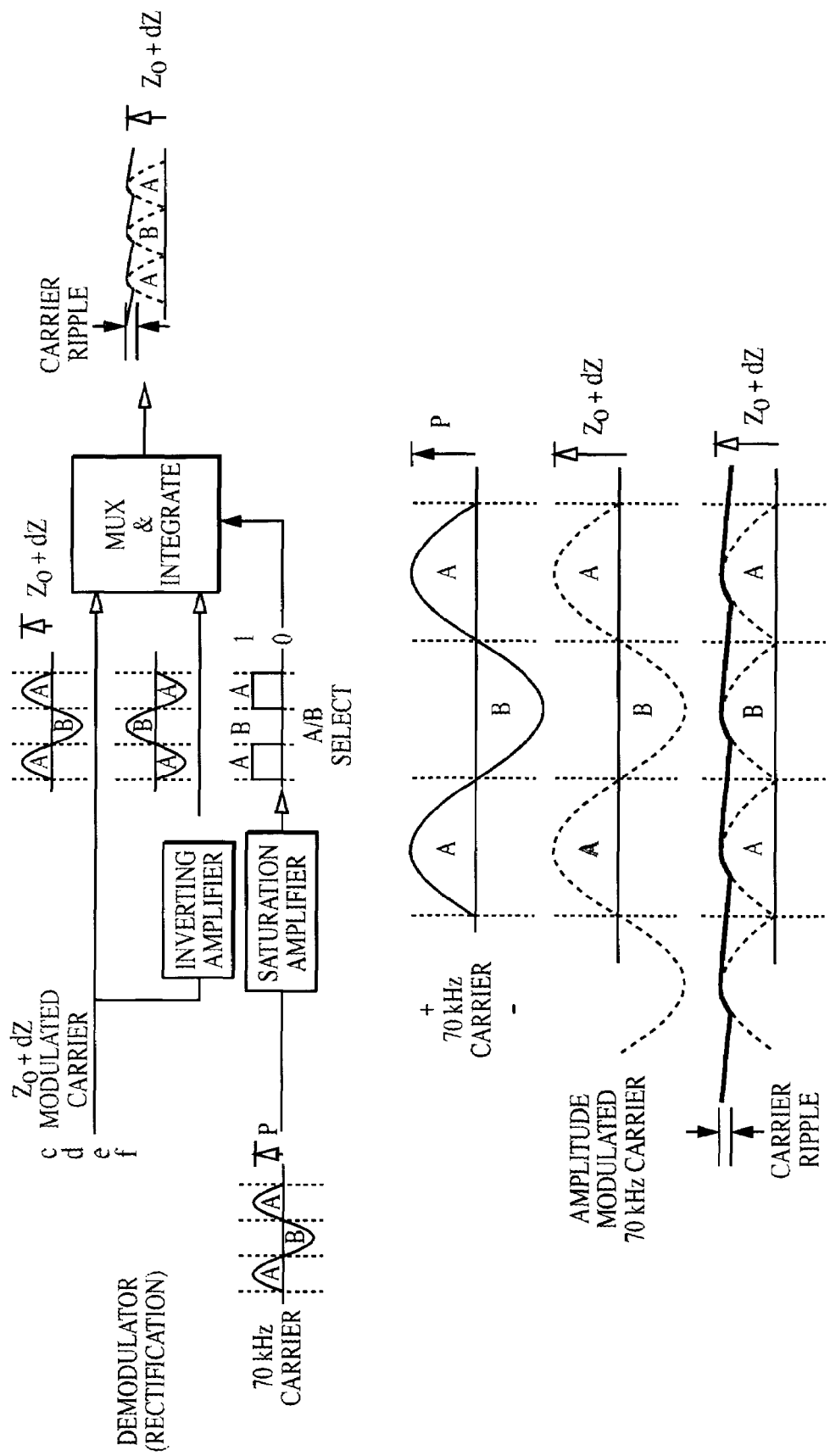
FIG. 13a is a graphical representation of the impedance signal extraction process performed by the ICG module of the present invention.

FIG. 13a graphically illustrates the impedance signal extraction process performed by the ICG module 1200 of the present invention.

In the illustrated embodiment of FIG. 13, the microprocessor 1206 comprises a microcomputer running at a crystal frequency of approximately 32.7 KHz, although it will be recognized that other platforms may be substituted with equal success. The system clock is generated by an on-chip phase-locked loop (PLL) and is software programmed for an operating frequency of 16 MHz. The device is operated in the 8-bit bus operating mode with all data transfers occurring on data lines 8 through 15. The processor also has a QSPI built in, which in the present embodiment is used for communications to the host device, such as by using a serial interface protocol of the type previously referenced herein.

The ICG module 1200 utilizes a three-part software architecture comprising three modules: (i) "Initialization" module; (ii) "Operating" module; and (iii) "Processing" module. Any one of the three software code modules can be independently downloaded.

The Initialization operating system of the microprocessor 1206 comprises a variant of the "C Executive" system manufactured by JMI Software Consultants, Inc., although it will be recognized that other operating systems may be substituted. C Executive comprises a real-time, memory-resident, event driven monitor program designed for embedded systems which require multi-tasking functionality and ROM storage. The initialization module software uses the initialization OS for process scheduling, input and output, and inter-process communication.

Figure 13B:
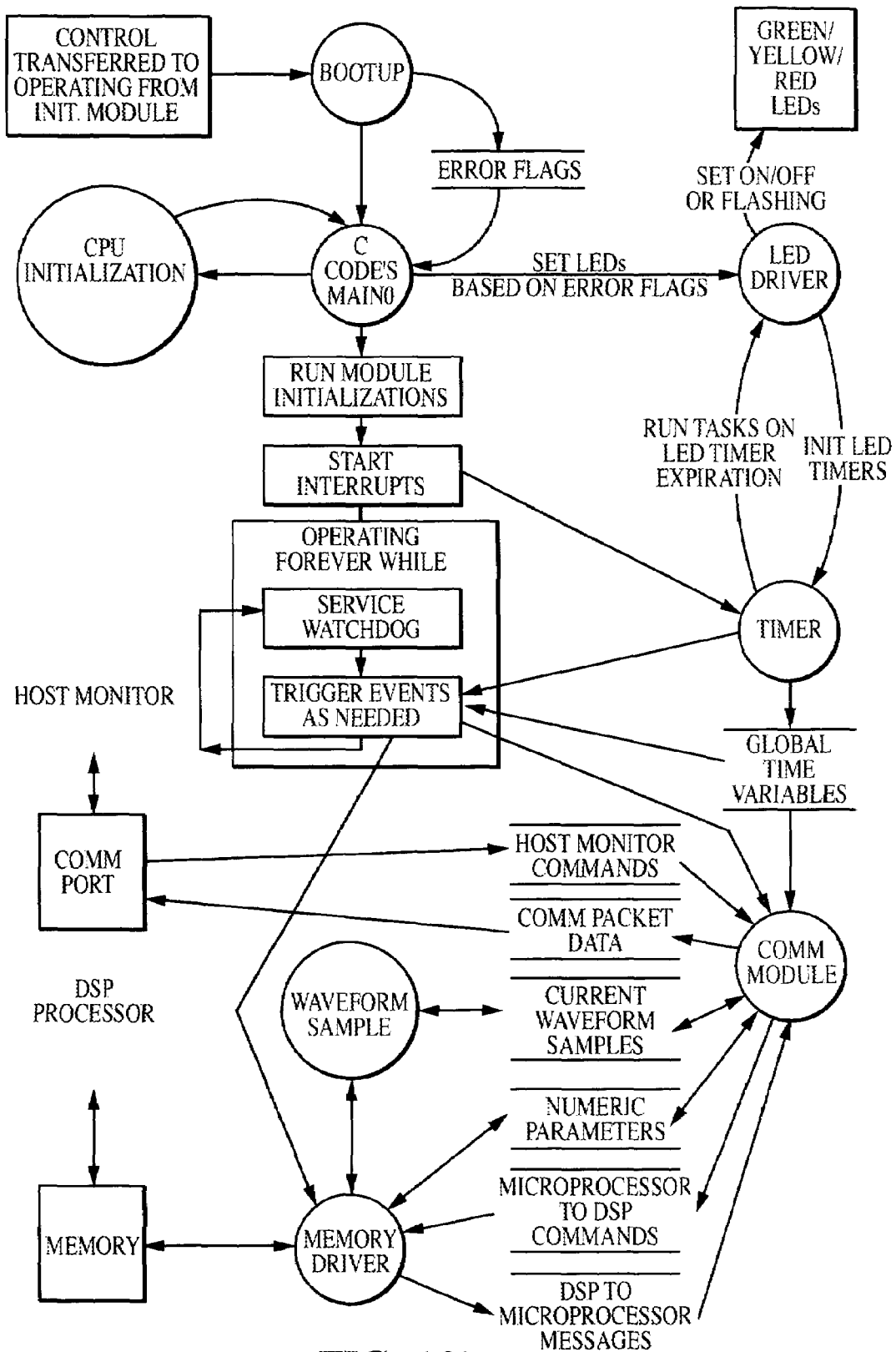
FIG. 13b is a logical flow diagram illustrating the Operating module program flow within the microprocessor of the ICG module of FIG. 13.

The processor Operating code does not use any operating system. Upon booting, the microprocessor registers are set for proper operation. Chip selects, interrupts, internal memory, stack pointer and initial program counter are all the responsibility of the Operating module's boot process. FIG. 13b graphically illustrates the high-level program flow of the Operating software module of the illustrated embodiment.

The processing module executes the bioimpedance algorithms. It also controls peripheral functions, such as the gain of the impedance amplifiers, the setting the ECG vector, reading of the impedance and ECG A/D converters, and detection of electrical continuity. The DSP 1210 of the invention comprises an Analog Devices ADSP-2181 device, although it will be recognized that any digital processing device adapted for algorithms such as those described herein may be used with proper adaptation. For example, members of the Texas Instruments 'C4x family of floating point DSPs, 'C5x family of fixed point processors, 'C6x family of VLIW processors, the Lucent DSP 16000 family, or even a user-customized processor core or ASIC may be used. Many other types of digital signal processors exist, any number of which may be adapted for use with the present invention.

Figure 13C:
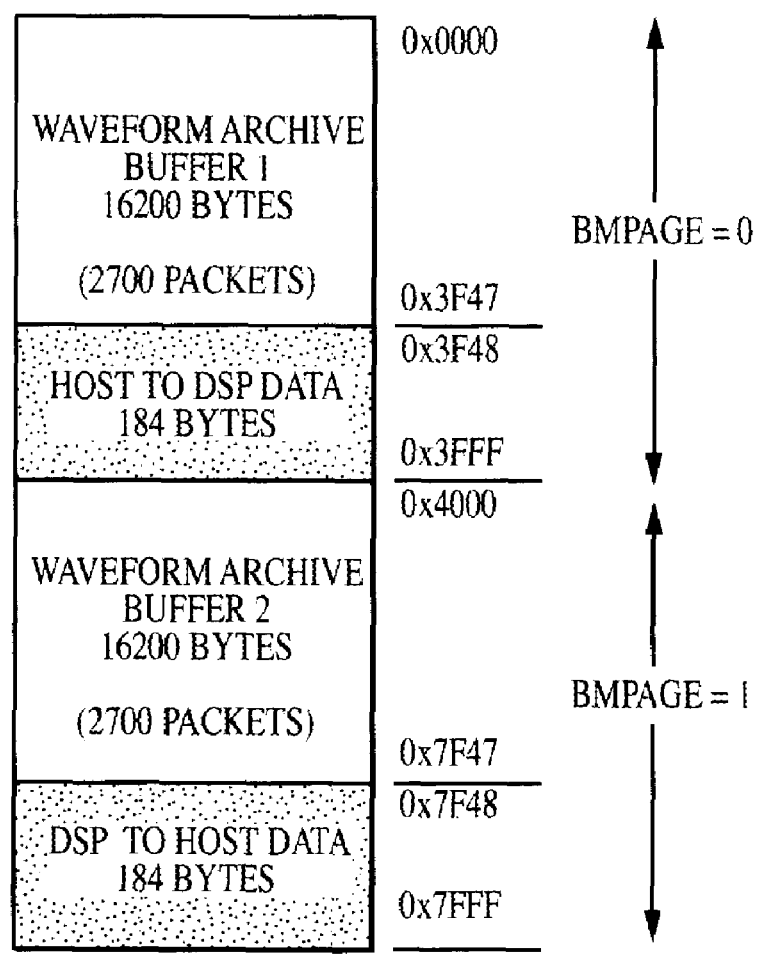
FIG. 13c is a graphical representation of one exemplary memory map used with the storage device of the processor board of FIG. 13.

Parameters determined from the digitized data are communicated to the microprocessor 1206 via the storage device 1208, specifically by writing data words to predetermined locations within the storage device. In the present embodiment, a dual-port RAM (DPR) is selected to allow dual-port access and two-way communication by the DSP 1210 (via, e.g., the BDM port) and microprocessor 1206 via first and second memory ports, respectively; however, it will be recognized that other types and configurations of storage device including DRAM, SDRAM, SRAM, dual data rate synchronous DRAM (DDR-SDRAM), ROM, or even non-semiconductor storage devices may be substituted. The embodiment of FIG. 13 further comprises a DMA unit of the type well known in the art, thereby facilitating direct memory accesses by the processor(s). The module 1200 is further configured such that address and data bus interfaces exist between the microprocessor 1206 and storage device 1208, and between the DSP 1210 and storage device 1208, thereby providing for memory addressing and data transfer by both processors. FIG. 13*c* illustrates one exemplary embodiment of the memory map used with the DPR 1208 of the ICG module.

An address range is also specified at the microprocessor 1206 and connected to the DSP's DMA port 1350 for DSP code download from the microprocessor 1206 (and host 1202) to the DSP 1210 during operation.

The impedance and ECG waveform data present within the module consists of all measured and calculated parameters related to a specific cardiac event, without any averaging. The start of data is placed at the Q point of the cardiac cycle measured. Waveform data is stored in the order shown in Table 1:

TABLE 1

| Byte | Value | Description |
|---|---|---|
| 0 | Start_data | Framing byte = 0xff |
| 1 | Error_status | Error codes for cardiac cycle |
| 2 | DSP Version integer | XX.00 |
| 3 | DSP Version fraction | 0.XX |
| 4 | ECG full scale range MSB | |
| 5 | ECG full scale range LSB | |
| 6 | ΔZ full scale range MSB | |
| 7 | ΔZ full scale range LSB | |
| 8 | R-R interval MSB | Ms |
| 9 | R-R interval LSB | |
| 10 | PEP MSB | Ms |
| 11 | PEP LSB | |
| 12 | LVET MSB | Ms |
| 13 | LVET LSB | |
| 14 | Predicted LVET MSB | Ms |
| 15 | Predicted LVET LSB | |
| 16 | Base Impedance MSB | Ωx100 |
| 17 | Base Impedance LSB | |
| 18 | Integral MSB | ΔZ integral * 100000 |
| 19 | Integral LSB | |
| 20 | Baseline MSB | ΔZ baseline value for Integral |
| 21 | Baseline LSB | |
| 22 | $\frac{dZ(t)}{dt_{max}} / Z_0$ MSB | value* 10000 |
| 23 | $\frac{dZ(t)}{dt_{max}} / Z_0$ LSB | |
| 24 | $\frac{d^2Z(t)}{dt^2_{max}} / Z_0$ MSB | value* 1000 |
| 25 | $\frac{d^2Z(t)}{dt^2_{max}} / Z_0$ LSB | |

TABLE 1-continued

| Byte | Value | Description |
|---|---|---|
| 26 | Ideal Weight MSB | Kg × 100 |
| 27 | Ideal Weight LSB | |
| 28 | R wave dv/dt detection threshold MSB | Samples |
| 29 | R wave dv/dt detection threshold LSB | |
| 30 | Pacer dv/dt detection threshold MSB | Samples |
| 31 | Pacer dv/dt detection threshold LSB | |
| 32 | Gender | 0 = male, 1 = female |
| 33 | Height | Cm |
| 34 | Weight | Kg |
| 35 | Body frame | 0 = small, 1 = medium, 2 = large |
| 36 | Age | Years |
| 37 | MAP | MmHg |
| 38 | Systolic Pressure | MmHg |
| 39 | Diastolic Pressure | MmHg |
| 40 | CVP | MmHg |
| 41 | PAOP | MmHg |
| 42 | Display Update Rate | 1-60 cycles |
| 43 | Cycle Averaging | 1-60 cycles |
| 44 | ECG Vector | 0 = EF, 1 = CF, 2 = DF, 3 = ED |
| 45 | Waveform Buffer Configuration | |
| 46 | Demo Waveform Flag | 0 = OFF, 1 = ON |
| 47 | Pacer Detection | 0 = OFF, 1 = ON |
| 48 | Electrode configuration | 0 = average, 1 = left, 2 = right |
| 49 | End data | Framing byte = 0xff |

So-called "live" waveform data is written into memory 1208 at a predetermined rate and at predetermined addresses to facilitate subsequent analysis; Table 2 illustrates the data write operations into memory performed by the DSP 1210 at a 200 Hz rate:

TABLE 2

| Data | Memory address | Description |
|---|---|---|
| ΔZ | 7FA0 | |
| ECG | 7FA2 | |
| Respiration | 7FA4 | |
| dZ/dt | 7FA6 | |
| pacer impulse | 7FA8 | |
| Pace enhanced ECG | 7FAA | ECG + pacer spikes |
| ECG gain factor | 7FAC | |
| Loose Electrode | 7FAE | |

The module 1200 further utilizes a 512K×8 static RAM (SRAM) array for temporary data storage. The static RAM is also used as temporary storage of ICG Monitor program code during program download of the software. The program code is stored in a 128K×8 sectored "flash" EPROM. This device can be erased on an individual sector basis. The first sector of the flash memory is used for storing the initialization (boot-up) code. In general, this sector of code is not modified, thereby ensuring that even if a download of code fails, the module will still be able to attempt another download. The other seven sectors of the flash memory are used for storage of the Operating code. As previously described below, the Operating code is the code which is run during normal operation of the module. This code can be updated using the host monitor or other external storage device.

The DSP 1210 of the present embodiment is also configured to receive a variety of useful data from the host/interface, as set forth in Table 3 below:

TABLE 3

| Data | Example DPR address | Description |
| --- | --- | --- |
| Gender | 3F50 | 0x0000 = male |
| | | 0x0001 = female |
| Height | 3F52 | Centimeters |
| Weight | 3F54 | Kilograms |
| Body Type | 3F56 | 0x0000 = small |
| | | 0x0001 = medium |
| | | 0x0002 = large |
| Age | 3F58 | Years |
| MAP | 3F5A | MmHg |
| Systolic | 3F5C | MmHg |
| Diastolic | 3F5E | MmHg |
| CVP | 3F60 | MmHg |
| PAOP | 3F62 | MmHg |

Figure 13D:
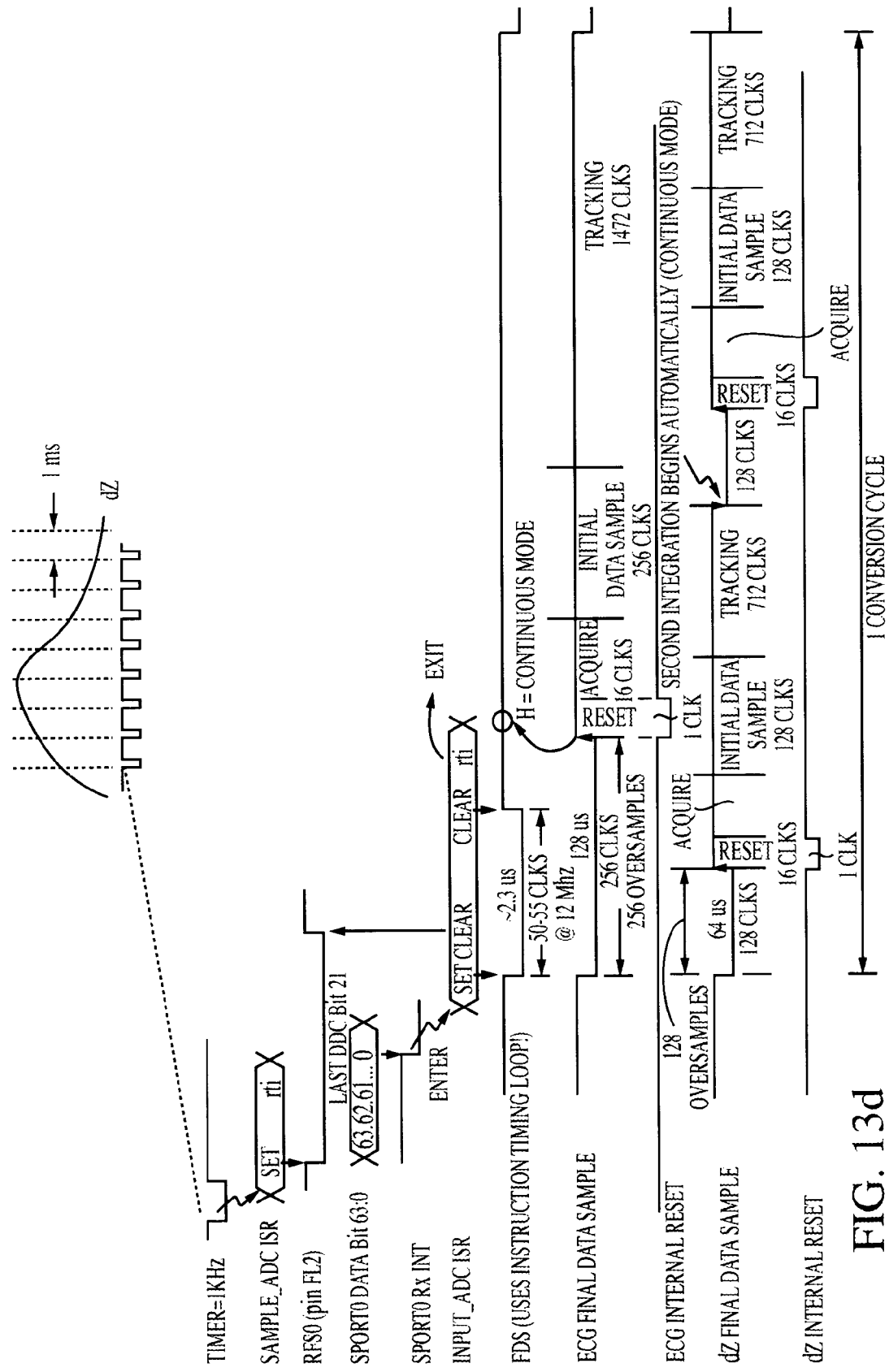
FIG. 13d is a graphical representation of the DSP port (e.g., SPORT0) and ADC data acquisition and timing relationships of the module of FIG. 12.

Other ports on the DSP 1210 are used for various functions in the module. For example, the SPORT0 is a standard port of the DSP which is used to transmit setup control to the ADCs 1313a, 1313b, 1319, digital potentiometers 1311a, 1311b, and the crosspoint switch, and receive data from the ADCs. DSP port SPORT1 is used to transmit data to the DAC 1334. FIG. 13d graphically illustrates the SPORT0 and ADC data acquisition and timing relationships of the present embodiment in detail.

Figure 14:
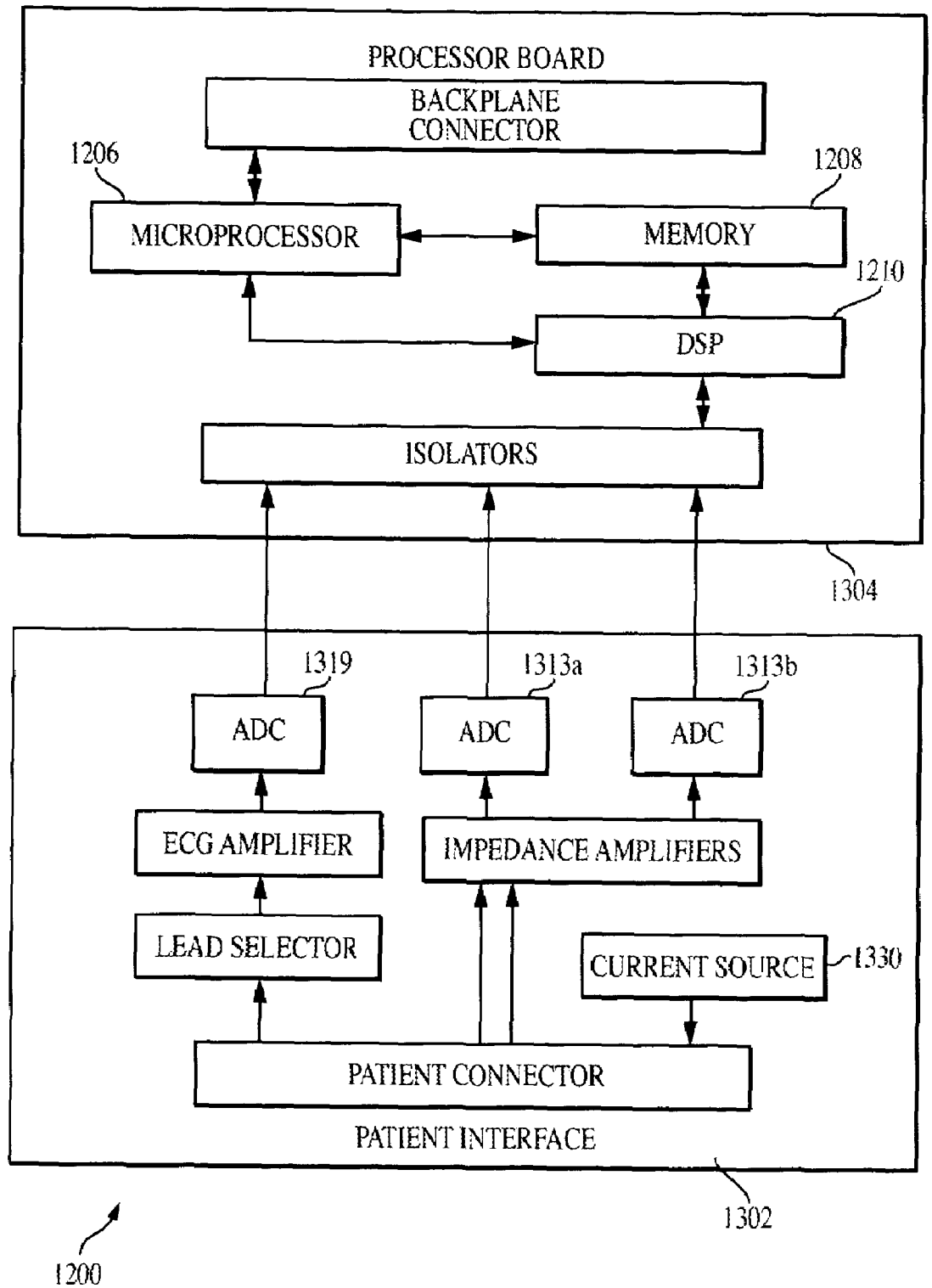
FIG. 14 is functional block diagram illustrating the data flow within the ICG module of FIGS. 12–13.

FIG. 14 illustrates portions of the data and signal flow within and between the patient and processor boards (and associated components) of the ICG module of FIGS. 12–13.

Appendix I hereto provides a listing of the various parameters utilized within or generated by the ICG module 1200. Note that the VEPT (Volume of Electrically Participating Tissue) and BSA (Body Surface Area) are, according to the present methodology, determined using the sex, height and weight of the patient measured, although other approaches may be substituted. Hemodynamic parameters are calculated from the values HR, PEP, VET, TFI, $$\frac{dZ(t)}{dt_{max}}$$

and $$\frac{d^2Z(t)}{dt^2_{max}}$$

which are extracted from the aforementioned ECG, $$\frac{dZ(t)}{dt}$$

and $$\frac{d^2Z(t)}{dt^2}$$

waveforms. Indexed parameters are obtained by dividing the parameter (e.g., BSA, CO, CI, SI) by the appropriate index.

Appendix II details the communications protocol (including memory address) for the patient data communicated by the exemplary embodiment of the module to the host device.

Fiducial Point Detection

Two important parameters present in estimations of cardiac output are (i) the maximum negative change in the impedance signal (Z(t)) as a function of time, $$\frac{dZ(t)}{dt_{max}};$$

and (ii) the ventricular ejection time (VET). These parameters, as well as other related parameters, are found from features referred to as "fiducial points" that are present in the inverted first derivative of the impedance waveform, $$\frac{dZ(t)}{dt}.$$

For example, the maximum value of $$\frac{dZ(t)}{dt},$$

referred to as $$\frac{dZ(t)}{dt_{max}},$$

is generally determined from the time at which the inverted derivative value has the highest amplitude, also commonly referred to as the "C point". The value of $$\frac{dZ(k)}{dt_{max}}$$

is calculated as this amplitude value. VET (also known as LVET, relating to the left ventricle of the heart in a human) corresponds generally to the time during which the aortic valve is open. That point in time associated with aortic valve opening, also commonly known as the "B point", is generally determined as the time associated with the onset of the rapid upstroke (a slight inflection) in $$\frac{dZ(t)}{dt}$$

before the occurrence of the C point. The time associated with aortic valve closing, also known as the "X point", is generally determined as the time associated with the inverted derivative global minimum, which occurs after the C point.

In addition to the foregoing "B", "C", and "X" points, the so-called "O point" may be of utility in the analysis of the cardiac muscle. The O point represents the time of opening of the mitral valve of the heart. The O point is generally determined as the time associated with the first peak after the X point. The time difference between aortic valve closing and mitral valve opening is known as the iso-volumetric relaxation time, IVRT.

Impedance cardiography further requires recording of the subject's electrocardiogram (ECG) in conjunction with the thoracic impedance waveform previously described. Processing of the impedance waveform for hemodynamic analysis requires the use of ECG fiducial points as landmarks. Processing of the impedance waveform is generally performed on a beat-by-beat basis, with the ECG being used for beat detection. In addition, detection of some fiducial points of the impedance signal may require the use of ECG fiducial points as landmarks. Specifically, individual beats are identified by detecting the presence of QRS complexes within the ECG. The peak of the R wave (commonly referred to as the "R point") in the QRS complex is also detected, as well as the onset of depolarization of the QRS complex ("Q point"). In patients with a pacemaker, the natural process of ventricular depolarization is either supplemented or entirely overridden.

Accordingly, in another embodiment, the ICG module of the present invention is further modified to incorporate fiducial point detection within the aforementioned impedance and/or ECG waveforms provided as inputs to the module. Specifically, "event markers" are placed within the waveform buffers to indicate the algorithm detection points with reference to the waveform samples. Table 3 below shows some of the marker values used for the various fiducial points:

TABLE 3

| Fiducial Point | Marker Value |
| --- | --- |
| Q point | 0x10 |
| B point | 0x20 |
| X point | 0x30 |
| dZ/dt max | 0x50 |
| d²Z/dt² max | 0x60 |

The difference between each detected X and B point is used to calculate ventricular ejection time (LVET). The magnitude of the largest negative derivative of the impedance change occurring during systole ($dZ/dt_{max}$) is calculated from the C point. LVET and $dZ/dt_{max}$ are then used to calculate the stroke volume, from which cardiac output (CO) is derived.

In yet another variant, fiducial point detection within the ICG module is conducted using the wavelet transform methodology as disclosed in co-pending U.S. patent application Ser. No. 09/764,589, entitled "Method And Apparatus For Hemodynamic Assessment Including Fiducial Point Detection", filed Jan. 17, 2001, assigned to the Assignee hereof, and incorporated herein by reference in its entirety herein. The fiducial points of the ΔZ and dZ/dt waveforms (e.g., B, C, X, and O) are detected in this variant using discrete wavelet transforms, rather than by empirical detection, which is based on processing features in the first and second derivatives of ΔZ(t). The wavelet transform methodology advantageously requires only simple additions and multiplications of real numbers, thereby substantially simplifying the processing associated with the cardiac output (CO) determination performed by the DSP 1210 and associated algorithms. Furthermore, the wavelet transform methodology, compared to the empirical methodology, is much less sensitive to noise artifact.

Similarly, fiducial points are utilized in evaluating the electrocardiogram (ECG) waveform of the subject, with specific individual "beats" of the subject's cardiac muscle being identified through detection of one or more fiducial points, either by the aforementioned wavelet transforms or by other means. The peak of the R wave (R point) in the QRS complex as well as the onset of depolarization of the QRS complex (Q point) are also detected. The time interval between the R waves is also used to calculate the subject's heart rate.

Alternate ICG Module Configurations

Referring now to FIGS. 15*a–c*, one embodiment of the ICG module of the present invention adapted for rack mounting is described. As shown in FIG. 15, the module 1500 is fitted with a faceplate 1502 disposed generally at the front portion 1506 of the module housing 1504, as well as a plurality of electrical connectors 1510, 1512, one connector 1510 disposed generally at the front portion 1506 of the housing, and one connector 1512 at the rear portion 1515 of the housing 1504. A debug port connector 1207 is also provided to facilitate debug of the microprocessor 1206. Optional module status indicators 1520 are also disposed on the faceplate 1502 so as to be viewable by a user or clinician during operation of the module when the module is received within an equipment "rack" (described in greater detail below). In the illustrated embodiment, the module housing 1504 is shaped and sized so as to be received within the rack adjacent or generally in proximity to other modules, such that space is economized.

The front panel connector 1510 comprises the ICG module interface with the patient being monitored, including electrical connection to the measurement and stimulation electrode terminals previously described herein. The front panel connector 1510 may be of any configuration, such as a multi-pin standardized male or female electrical connector of the type well known in the art, although literally any configuration (proprietary or otherwise) may be substituted.

The rear panel connector 1512 allows for electrical connection of the module to the host monitor/interface unit, such as for example via a multi-pin female connector for mating with backplane connectors of the host monitoring equipment (including any voltage supply associated therewith). It will be recognized, however, that other types and "pin-outs" of connector or data/power interface may be substituted with equal success, dependent primarily on the host equipment with which the module must interface.

The equipment module 1500 of FIG. 15 may also be configured with a network data interface (described in detail below with respect to FIG. 19), thereby allowing the distribution of data to a plurality of different local and/or remote nodes for analysis, storage, or other functions.

Figure 16:
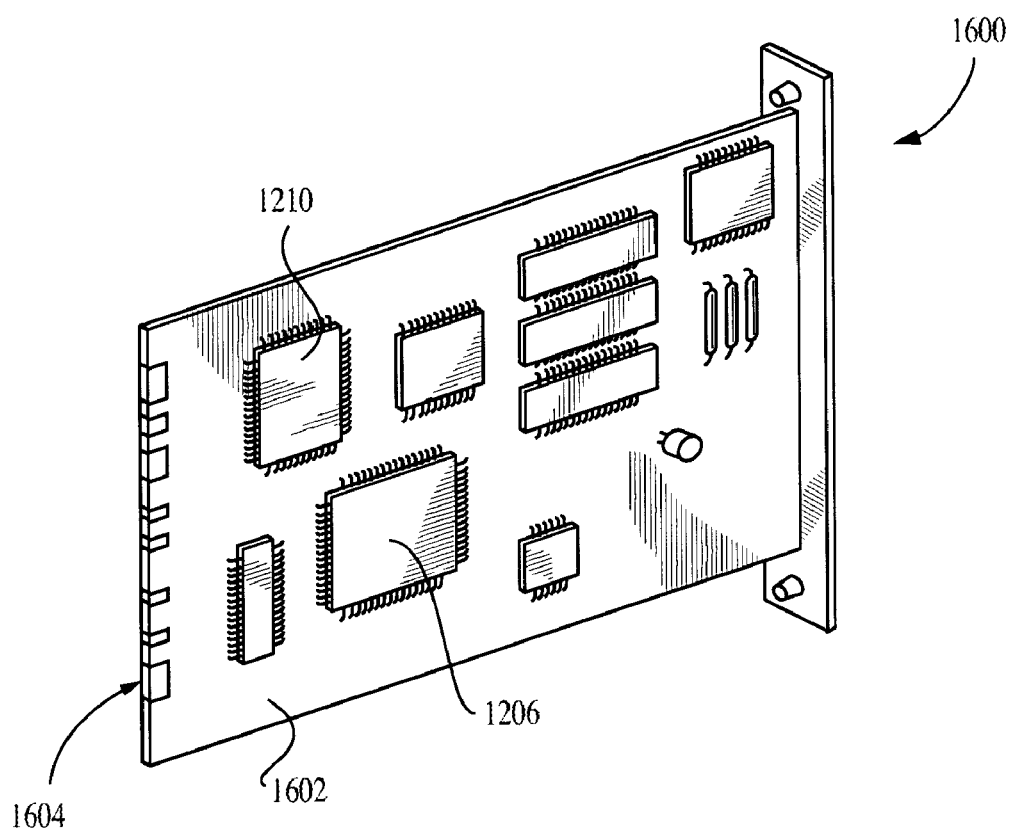
FIG. 16 is a perspective view of the module of FIGS. 12–14, configured as a plug-in circuit card for use within a host device.
Figure 17:
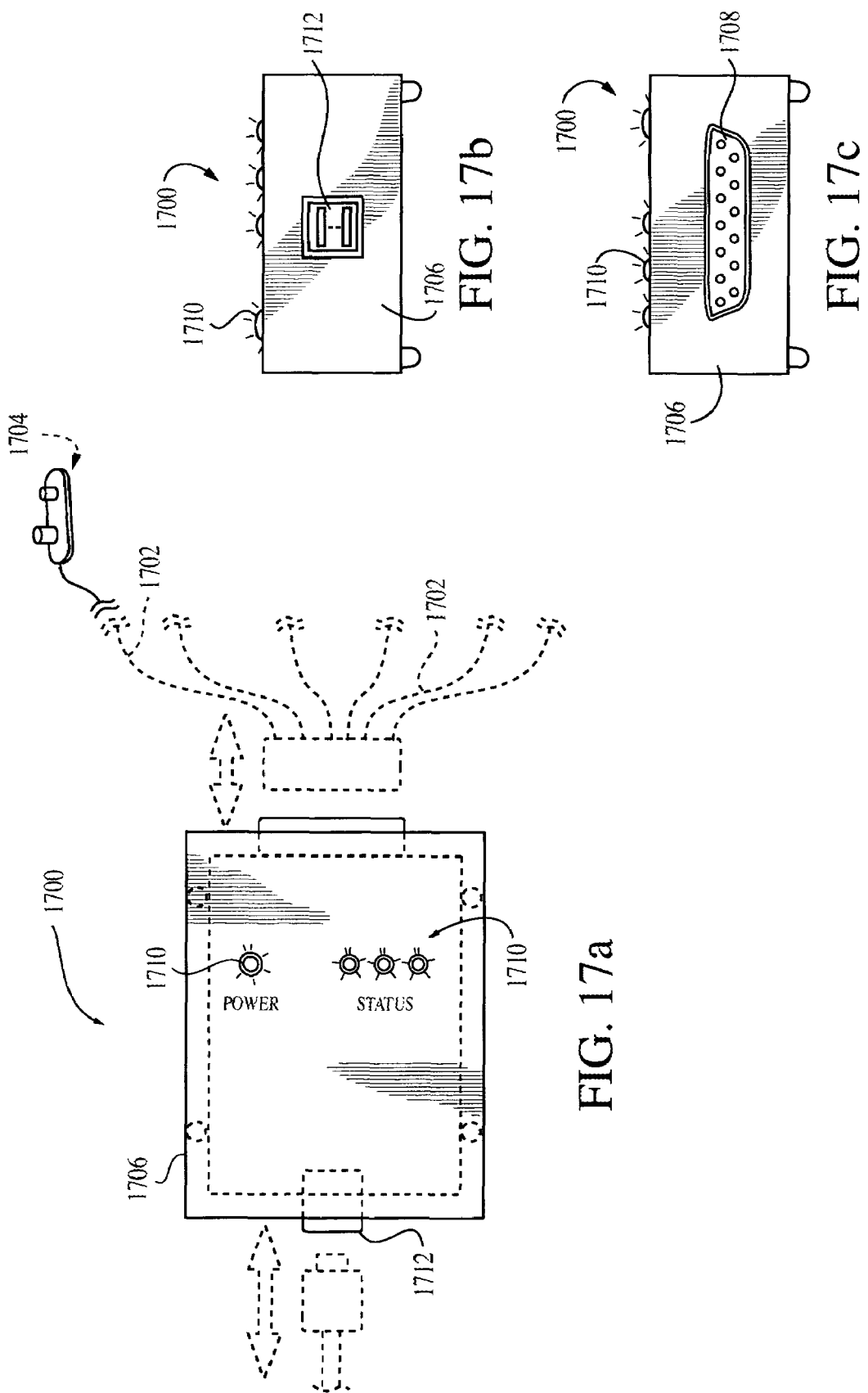
FIGS. 17a–c are top, rear, and front plan views, respectively, of the module of FIGS. 12–14, configured as a yoke adapted for mobility and electrical interface with a monitoring device.

FIG. 16 illustrates yet another embodiment of the ICG module of the invention, configured as a plug-in circuit card 1600 for use within a host device such as a dedicated stand-alone monitor or host monitoring device (e.g., one that has a primary function which may or may not be related to ICG or cardiography), personal computer, laptop computer, hand-held computer, minicomputer, or SUN UNIX workstation. The circuit card 1600 integrates all of the functionality of the embodiment of FIG. 1300, including processor and patient interface boards, onto one card substrate 1602. A standardized edge-type electrical connector 1604 is also provided to permit interface with the card receptacle of the host device (not shown), which may be configured according to any electrical interface standard (such PCMCIA, PC Card, or otherwise).

In yet another embodiment (not shown), the ICG module of the invention comprises a card generally similar to that shown in FIG. 16, except that the edge-type connector 1604 is replaced with a ribbon-cable and associated connector (or other type of connector) of the type well known in the electrical arts for interfacing the module with other circuit elements and boards within the host device. As yet another alternative, the ICG module may be plugged directly into another module within the host device. It will be recognized that literally any type of electrical interconnection scheme and protocol between the ICG module of the present invention (whether in "card" form as in FIG. 16 or otherwise) and the host device with which the module is used may be employed consistent with the invention.

FIGS. 17a–c illustrate yet another embodiment of the ICG module of the invention, configured as a "yoke" 1700 adapted for mobility and electrical interface with a monitoring device. As used herein, the term yoke is meant to include any configuration of mobile or transportable device which is used to facilitate centralization of a plurality of patient signals. In the present embodiment, the yoke 1700 is adapted to receive a plurality of electrical leads 1702 (whether as individual leads, in one variant, or as a single multi-terminal electrical connector 1708, in another variant) which are connected to the electrodes 1704 disposed on the thorax of the patient being monitored. The yoke 1700 is configured to be light weight and rugged, and utilizes a molded plastic impact-resistant housing 1706 of the type well known in the polymer arts, although other materials may be used. The yoke housing 1706 contains the electronics of the ICG module, including processor and patient interface boards (not shown), and further optionally includes an LED 1710 or other status indication for the ICG module. The output of the ICG module electronics in the yoke 1700 is transferred to the monitoring device (not shown) via a data interface 1712, in the present embodiment a universal serial bus (USB) connection and cable of the type well known in the electrical arts. This USB interface advantageously allows the yoke 1700 to interface data with any number of different types of devices, each of which include their own USB interface.

Alternatively, a wireless interface between the yoke 1700 and host monitor (or for that matter, between the yoke 1700 and the patient electrodes) may be used. For example, in one exemplary variant, an RF transceiver and modulator device are provided and adapted to generally comply with the well known "Bluetooth™" wireless interface standard. The Bluetooth "3G" wireless technology allows users to make wireless and instant connections between various communication devices, such as mobile devices (e.g., cellular telephones, PDAs, notebook computers, local or remote patient monitoring stations, and the like) and desktop computers or other fixed devices. The Bluetooth topology supports both point-to-point and point-to-multipoint connections. Multiple "slave" devices can be set to communicate with a 'master' device. In this fashion, the yoke 1700 of the present invention, when outfitted with a Bluetooth wireless suite, may communicate directly with other Bluetooth compliant mobile or fixed devices including a receiver disposed at the host monitor, or alternatively other Bluetooth-capable devices such as a cellular telephone, PDA, notebook computer, or desktop computer. Alternatively, WMTS telemetry may be utilized. The operation of the wireless interface is effectively transparent to the yoke 1700 and host monitor, although it will be recognized that data may be "buffered" within one or more intermediary storage devices (not shown) if desired.

Additionally, it will be recognized that for purposes of saving space within the yoke 1700, the signal processing and transceiver/modulator components of the interface may be embodied in a fully integrated "system on a chip" (SoC) application specific integrated circuit (ASIC) of the type generally known in the semiconductor fabrication arts (not shown). The SoC ASIC incorporates, inter alia, a digital signal processor (DSP) core, embedded program and data random access memories, RF transceiver circuitry, modulator, analog-to-digital converter (ADC), and analog interface circuitry necessary to support sampling, conversion, processing, and transmission of the cardiac output (or other) data to the host monitor's receiver.

Alternatively, a number of different subjects undergoing cardiac monitoring/analysis using the yoke 1700 of the present invention (or other comparable devices) may be monitored in real time at a centralized location using a single monitor receiver. Specifically, the monitor receiver (not shown) and transceiver are adapted to receive a plurality (currently seven, under prevailing Bluetooth architecture, although such number may be increased or decreased) of signals from remote ICG module devices, whereby the individual signals may be multiplexed or alternatively processed in parallel by the host monitor and interface (with the addition of appropriate multiplexing or parallel processing hardware of the type well known in the electronic arts). Hence, a host monitor configured to receive such multiplexed or parallel channel data may be used to monitor the cardiac output and other related parameters of multiple subjects at once.

Bluetooth-compliant devices, inter alia, operate in the 2.4 GHz ISM band. The ISM band is dedicated to unlicensed users, including medical facilities, thereby advantageously allowing for unrestricted spectral access. Maximum radiated power levels from the yoke's transceiver are in the mW range, thereby having no deleterious effect on the physiology of the subject due to radiated electromagnetic energy. As is well known in the wireless telecommunications art, radiated power from the antenna assembly (not shown) of the yoke transceiver may also be controlled and adjusted based on relative proximity of the transceiver, thereby further reducing electromagnetic whole body dose to the subject. The modulator of the yoke uses one or more variants of frequency shift keying, such as Gaussian Frequency Shift Keying (GFSK) or Gaussian Minimum Shift keying (GMSK) of the type well known in the art to modulate data onto the carrier(s), although other types of modulation (such as phase modulation or amplitude modulation) may be used.

Spectral access of the device may be accomplished via frequency divided multiple access (FDMA), frequency hopping spread spectrum (FHSS), direct sequence spread spectrum (DSSS, including code division multiple access) using a pseudo-noise spreading code, or even time division multiple access, depending on the needs of the user. For example, devices complying with IEEE Std. 802.11 may be substituted in the probe for the Bluetooth transceiver/modulator arrangement previously described if desired. Literally any wireless interface capable of accommodating the bandwidth requirements of the system may be used, such as the new WMTS biomedical band of 608–614 MHz. As yet another embodiment, an infrared device (e.g., Infrared Data Association "IrDA") may be substituted or even used in conjunction with the aforementioned wireless interface of the yoke.

Figure 18:
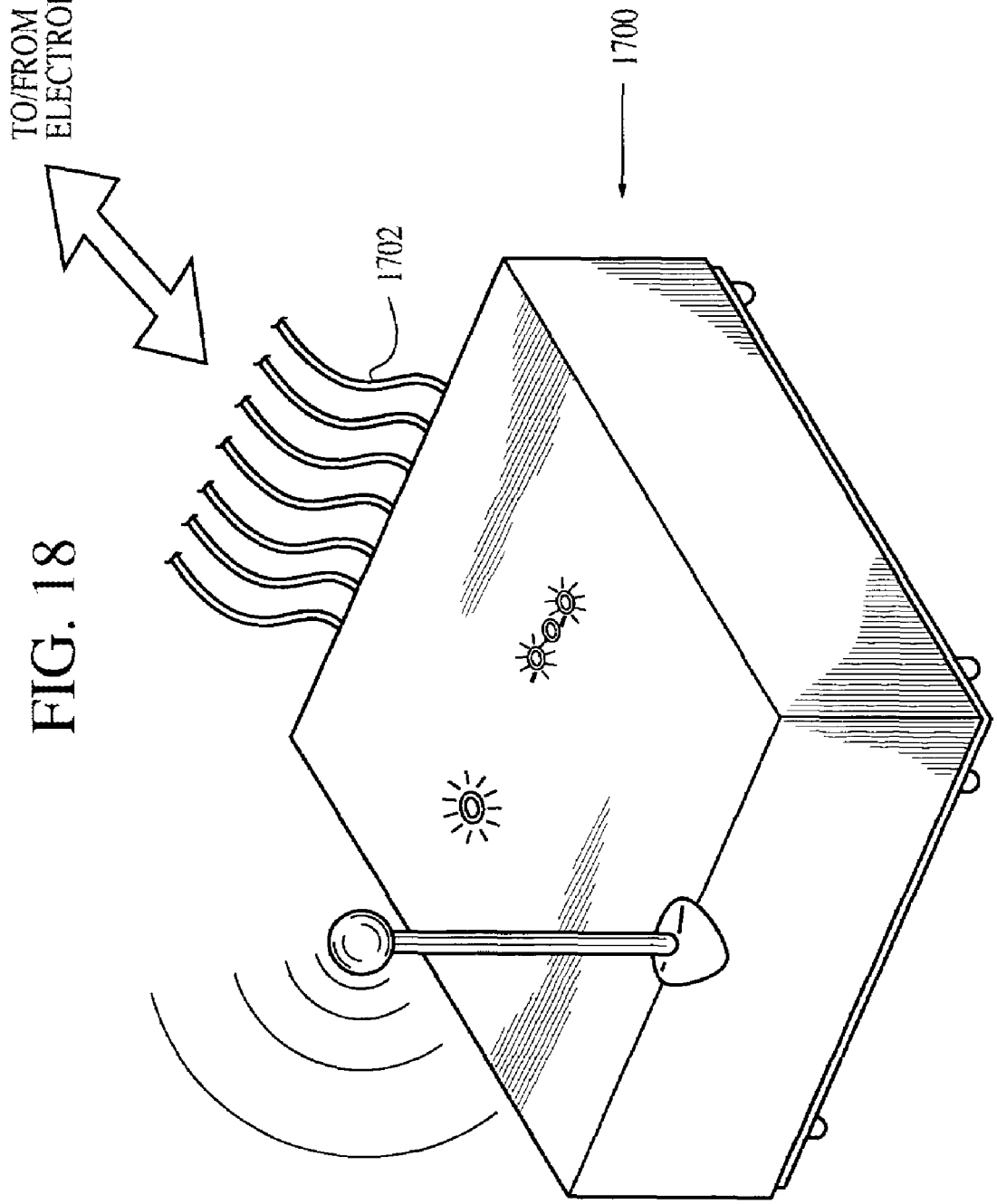
FIG. 18 is a perspective view of the yoke of FIGS. 17a–c, adapted for wireless communication with the monitoring device.

FIG. 18 is a perspective view of the yoke of FIGS. 17a–c, adapted for wireless communication with the monitoring device as just described.

Figure 19:
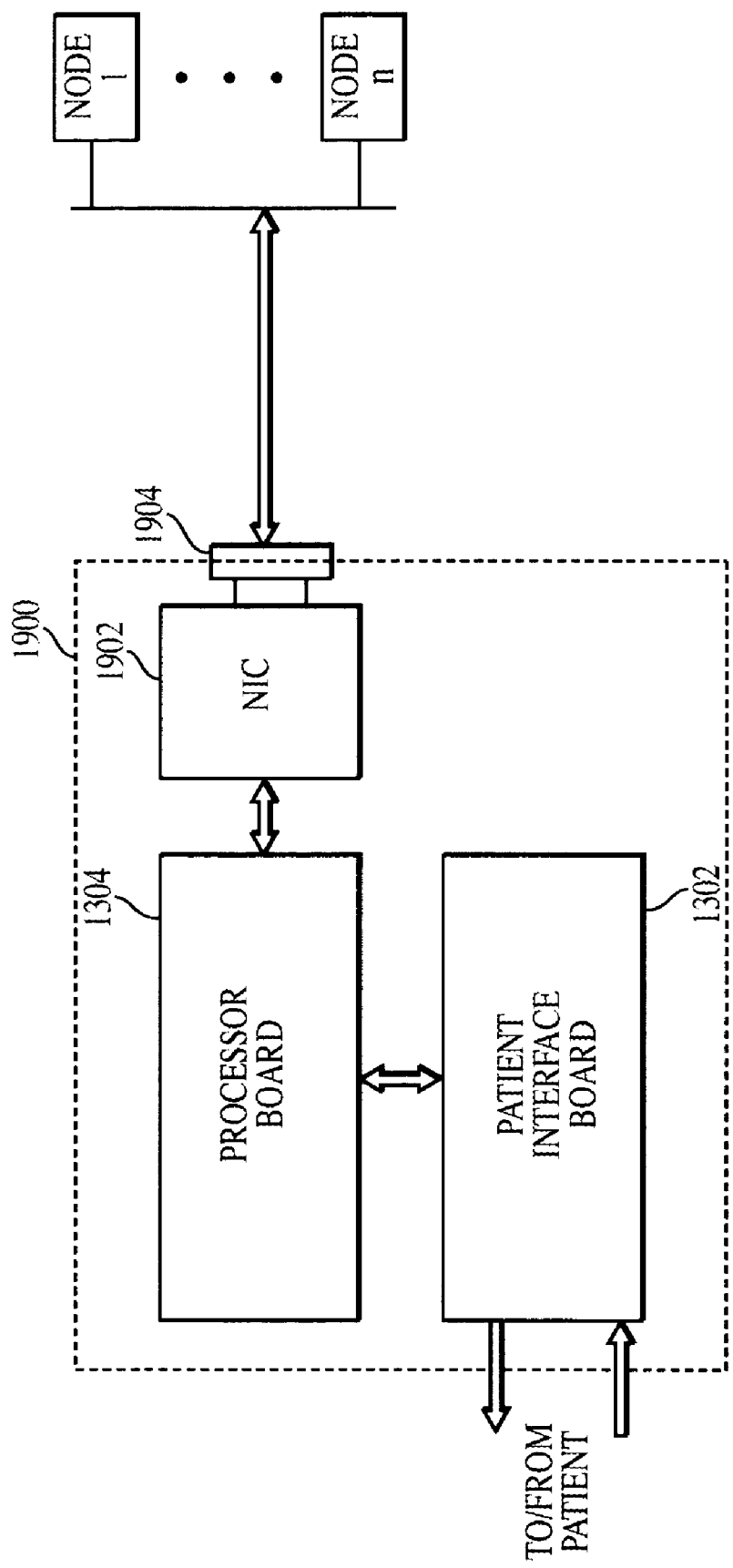
FIG. 19 is a block diagram of the module of FIGS. 12–14, including network interface and associated data network.

Referring now to FIG. 19, yet another embodiment of the ICG module of the invention is described, wherein the module 1900 is fitted with a network interface device 1902 (e.g., LAN card) and associated data network connector 1904. The network interface card 1902 and connector 1904 (including attendant NIC software running on the ICG microprocessor 1206) allow the cardiac output (CO) and other data generated by the module to be transferred to one or more remote nodes, such as the various stations of a local area network or wide area network. The network interface device 1902 in the present embodiment comprises an IEEE 802 Ethernet card adapted for packetized data transfer, although it will be recognized that any number of different network hardware environments (including, e.g., X.25, Token Ring, SONET, FDDI, Gibagbit Ethernet, or ATM) and protocols (e.g., TCP/IP, RTP, or FTP) may be utilized. In another embodiment (not shown), the ICG module may be outfitted with a modulator/demodulator apparatus of the type well known in the data communication arts, or DSL, ADSL, or DOCSIS device. Literally any data network device, including satellite uplink/downlink, can be used for transferring cardiac data to/from the ICG module consistent with the invention.

Input Vector Selection

The ICG module of the present invention includes provision, via the aforementioned patient board 1302, for receiving a plurality of input signals ("vectors") that may be used in the cardiac output determination. These input vectors typically include ECG signals that are derived, for example, from the various ICG/ECG electrodes disposed on the subject's body. Alternatively, such signal sources may comprise one or more other modules or devices. Regardless of source or type of signal, these input vectors may vary significantly in terms of signal quality and/or continuity. Therefore, the present invention is advantageously adapted to automatically (and continuously, if desired) analyze and arbitrate between the various input vectors based on their relative attributes (e.g., signal quality). This feature of the invention is now described in detail with respect to FIGS. 20–22.

As previously described with respect to FIG. 13, the ECG vector of the ICG module is selected using a vector select multiplexer 1315. In the embodiment of FIG. 13, the vector is selectable from a plurality of electrode pairs located at various points on the thorax of the subject, as shown in Table 4 below:

TABLE 4

| Vector | ECG Channel |
|---|---|
| 1 | EF |
| 2 | CF |
| 3 | DF |
| 4 | ED |

Figure 20:
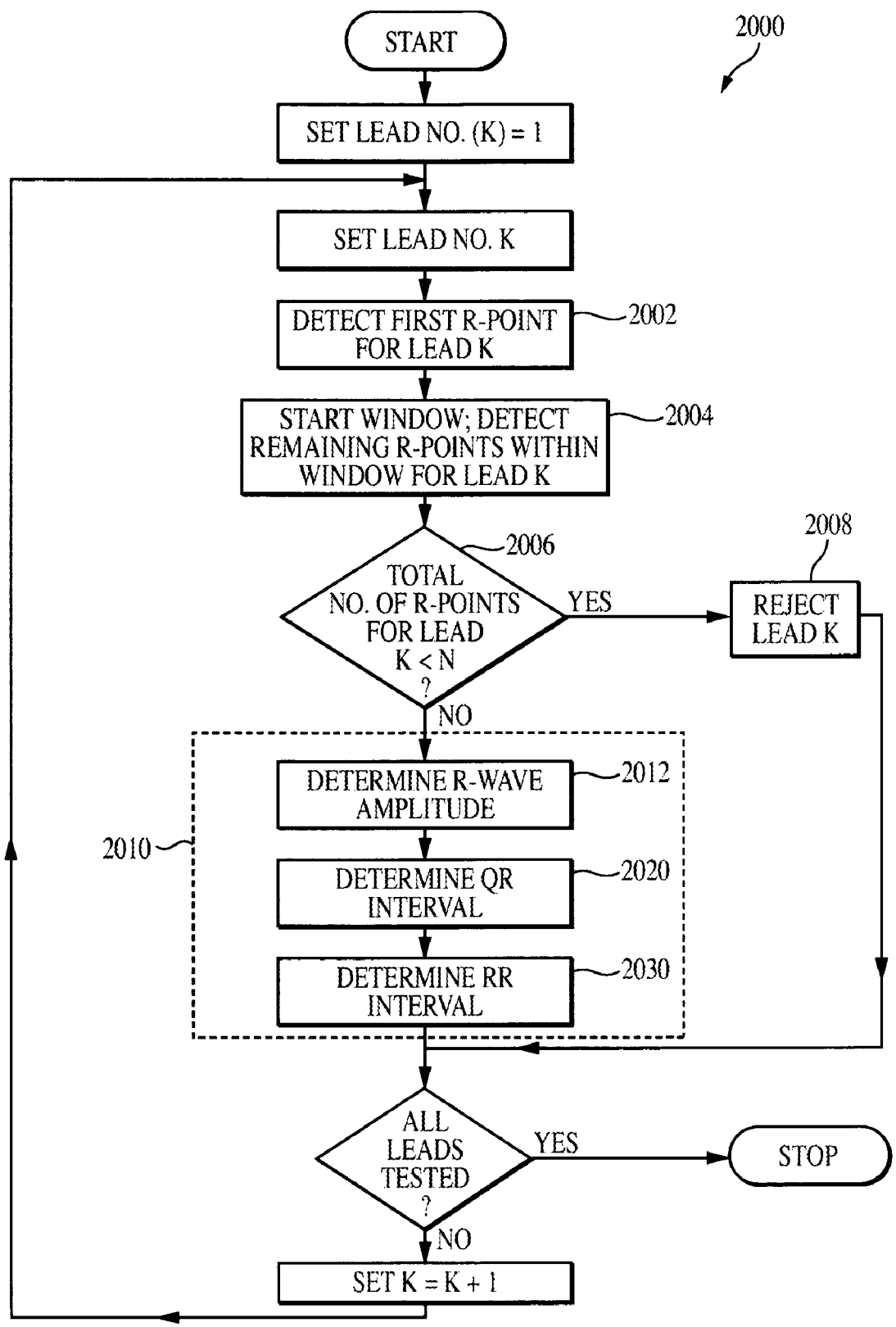
FIG. 20 is a logical flow diagram illustrating the methodology of auto-parameter (e.g., ECG) vector selection according to the invention.

FIG. 20 illustrates the methodology of ECG vector selection. It will be recognized that while the following discussion is drawn with respect to a plurality of ECG input vectors, other types of signals may be analyzed and arbitrated using the methodology of the invention.

In the first main step 2004 of the method of vector selection 2000, each electrical lead providing a signal input is tested within a predetermined (e.g., six second) time window, beginning at the first detected R point (step 2002) in the input vector under analysis. If the total number of R points detected within the window is less than a given value n (e.g., 4) per step 2006, the lead is rejected per step 2008.

Figure 20A:
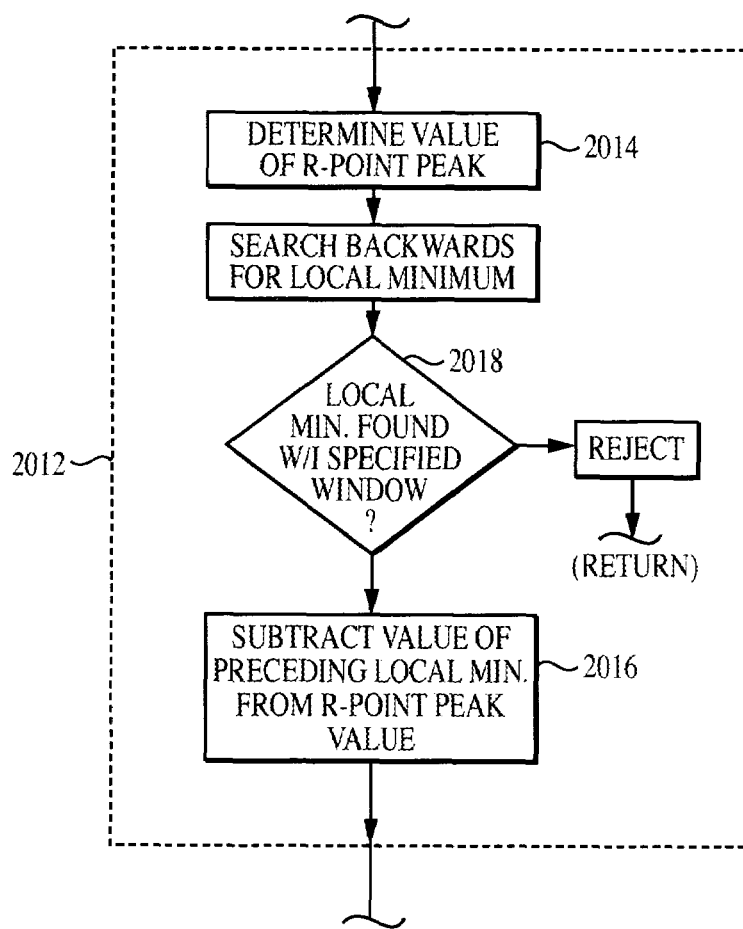
FIG. 20a is a logical flow diagram illustrating one exemplary method of determining the R-wave amplitude factor.

Additionally, each lead is evaluated per step 2010 of the present method 2000 based upon three factors: (i) R-wave magnitude, (ii) QR interval difference, and (iii) RR interval difference. R-wave magnitude (RM) is the peak-to-peak magnitude of the R point, which is calculated per step 2012 as shown in FIG. 20a by taking the value of the R peak (step 2014) and subtracting the value of the preceding local minimum (step 2016). If there is no local minimum found within a "back" sample or temporal window of a given size (e.g., 80 samples) per step 2018, the R point is rejected. FIG. 21 illustrates the calculation process graphically in terms of a typical QRS complex.

Figure 20B:
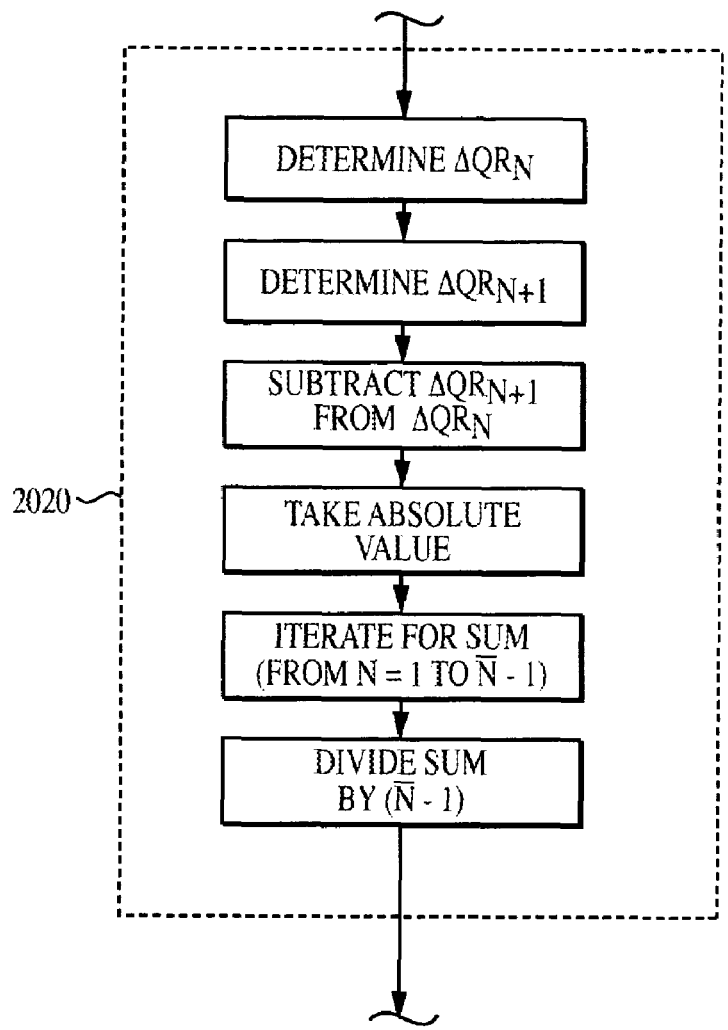
FIG. 20b is a logical flow diagram illustrating one exemplary method of determining the QR interval difference ($QR_{score}$) factor.
Figure 20C:
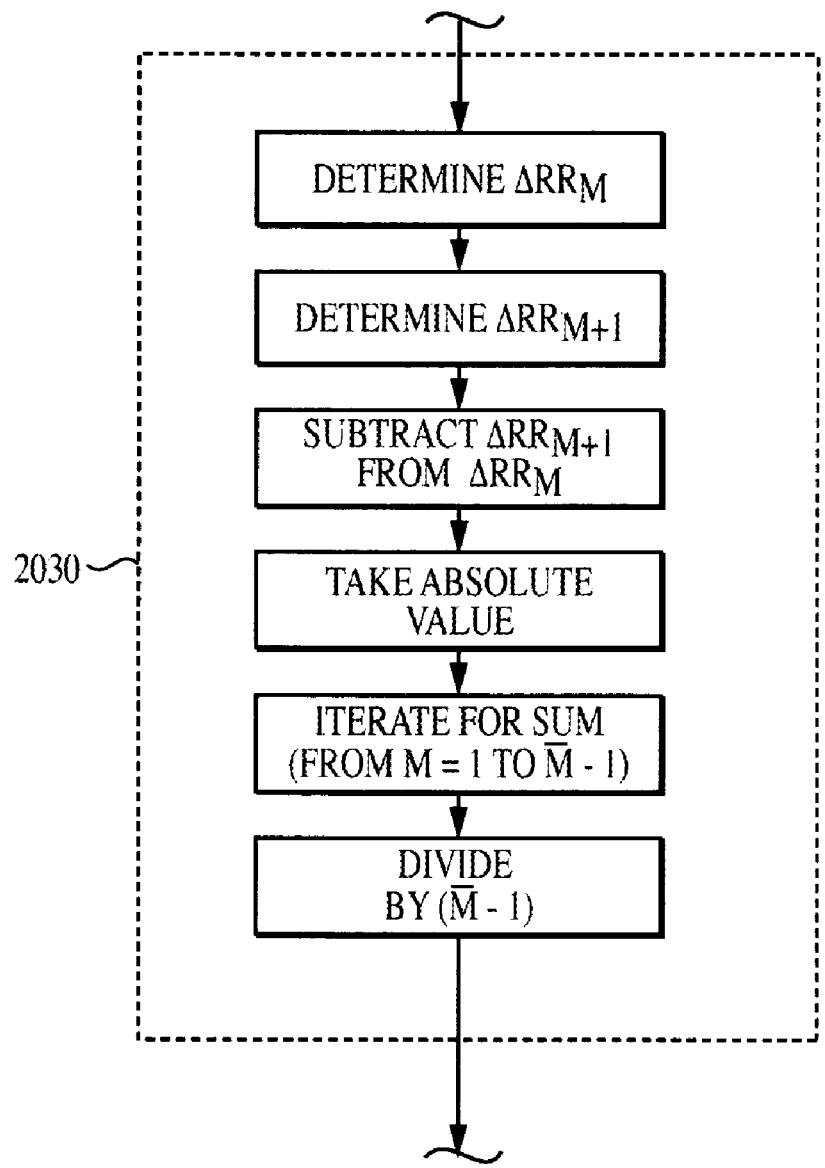
FIG. 20c is a logical flow diagram illustrating one exemplary method of determining the RR interval difference ($RR_{score}$) factor.

Next, the QR interval difference ($QR_{score}$) and the RR interval difference ($RR_{score}$) are determined per steps 2020 (FIG. 20b) and 2030 (FIG. 20c), respectively, as follows.

1. QR Interval Difference Score ($QR_{score}$)—The QR interval difference score is used to identify variability of feature detection within the QRS complex. This factor measures the time difference between the Q point and the R point, and compares this value to all other values detected within the given time window. FIG. 22 illustrates this process graphically (along with that of the R to R interval difference calculation, described below). Eqn. 5 defines this relationship mathematically:

$$QR_{score} = \frac{\sum_{n=1}^{N-1} ABS(\Delta QR_n - \Delta QR_{n+1})}{N-1};  \quad \text{(Eqn. 5)}$$

Where N=the number of R points detected within the selected time window, and $\Delta QR_n$ is the time from the Q point to the R point for the nth QRS complex detected.

2. RR Interval Difference Score ($RR_{score}$)—The RR interval difference score is used primarily to identify variability of detection between QRS complexes. This factor measures the time difference between one R point to the next R point. FIG. 22 illustrates this process graphically. Eqn. 6 defines this relationship mathematically:

$$RR_{score} = \frac{\sum_{m=1}^{M-1} ABS(\Delta RR_m - \Delta RR_{m+1})}{M-1};  \quad \text{(Eqn. 6)}$$

Where M=the number of QRS complex intervals detected within the selected time window, and $\Delta RR_m$ is the time from one R point to the next R point in the nth interval.

Each lead factor is also optionally normalized, to between 0 and 1 in the illustrated embodiment. For RM, all of the lead magnitudes are divided by the maximum value among the leads. For the $QR_{score}$ and $RR_{score}$ values, the number are first inverted, and then normalized based upon the maximum value among the leads. In the event there is zero variability between QR intervals or RR intervals, the value are set to a small constant before inversion (or, alternatively, any other approach which accounts for the infinite value when inverting zero may be employed). For example, the Assignee hereof has determined that optimal values to be used during testing are 0.01 and 0.3125 for $QR_{score}$ and $RR_{score}$, respectively, although other values may clearly be substituted.

The lead (vector) choice is based upon the maximum value of the sum total of the three factors for each lead. The normalization and selection algorithm is given by Eqn. 7:

$$\underset{1 \to 4}{\text{MAX}}\left\{\sum_{L=1}^{4}\left[\frac{RM_L}{\underset{1 \to 4}{\text{MAX}}(RM)} + \frac{(QR_{score})_L^{-1}}{\underset{1 \to 4}{\text{MAX}}((QR_{score})^{-1})} + \frac{(RR_{score})_L^{-1}}{\underset{1 \to 4}{\text{MAX}}((RR_{score})^{-1})}\right]\right\} \quad \text{(Eqn. 7)}$$

where L is the lead number (arbitrarily assigned), and the function $$\underset{1 \to 4}{\text{MAX}}(\ldots)$$

is the maximum value among the four leads. By default, the leads are ranked from best to worst as: Lead 2, Lead 3, Lead 1, and Lead 4. The default lead order is selected based upon an ideal mean electrical axis of the heart. Lead 2 should, theoretically, have the largest ECG amplitude because the electrical projection onto this lead is the greatest with the electrodes 'CF' used for the ECG. The other rankings are determined based upon this theory, using the expected relative voltage from the lead. If two or more leads have the same score, the lead is selected based upon this ranking system.

It will be appreciated that while a three-factor approach (i.e., R-wave amplitude, QR interval, and RR interval) is utilized, other types and number of factors may be substituted. For example, a two-factor summation of R-wave amplitude and QR-interval difference could be utilized. Furthermore, the quality determination need not rely on a summation; a mathematical factoring equation (i.e., where the individual quality factors or indexes are multiplied together to result in a single quality index) could be utilized with equal success. Many other such variations and permutations are possible consistent with the present invention, the embodiments illustrated herein being merely exemplary in nature.

It will be recognized that while certain aspects of the invention have been described in terms of a specific sequence of steps of a method, these descriptions are only illustrative of the broader methods of the invention, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the invention disclosed and claimed herein.

While the above detailed description has shown, described, and pointed out novel features of the invention as applied to various embodiments, it will be understood that various omissions, substitutions, and changes in the form and details of the device or process illustrated may be made by those skilled in the art without departing from the invention. The foregoing description is of the best mode presently contemplated of carrying out the invention. This description is in no way meant to be limiting, but rather should be taken as illustrative of the general principles of the invention. The scope of the invention should be determined with reference to the claims.

APPENDIX I

ICG MODULE PARAMETERS

| Abbreviation | Description of Parameter | Unit |
|---|---|---|
| ACI | Acceleration Index $= \dfrac{d^2Z(t)}{dt^2_{max}}\bigg/Z_o$ | $s^{-2}$ |
| BP | Blood Pressure | MmHg |
| BSA | Body Surface Area | $m^2$ |
| CI | Cardiac Index (CO divided by BSA) | L min$^{-1}$ m$^{-2}$ |
| CO | Cardiac Output | L min$^{-1}$ |
| CVP | Central Venous Pressure | MmHg |
| dZ/dt | First time-derivative of impedance Z | $\Omega$ s$^{-1}$ |
| $d^2Z/dt^2$ | Second time-derivative of impedance Z | $\Omega$ s$^{-2}$ |
| ECG | Electro Cardio Graph | Milli Volts/time |
| EDI | End-Diastolic Index (EDV divided by BSA) | ml m$^{-2}$ |
| EDV | End-Diastolic Volume | Ml |
| EF | Ejection Fraction | % |
| ER | Ejection Ratio | % |
| HR | Heart Rate | Bpm |
| IC | Index of Contractility $= \dfrac{dZ(t)}{dt_{max}}\bigg/Z_o$ | $s^{-1}$ |
| LCW | Left Cardiac Work | Kg m |
| LCWI | Left Cardiac Work Index | Kg m m$^{-2}$ |
| LSW | Left Stroke Work | G m |
| LSWI | Left Stroke Work Index | G m m$^{-2}$ |
| LVET | Left-Ventricular Ejection Time (also known as VET) | Ms |
| MAP | Mean Arterial Pressure | MmHg |
| PAP | Pulmonary Arterial Pressure | MmHg |
| PAOP | Pulmonary Artery Occluded Pressure | MmHg |
| PEP | Pre-Ejection Period | Ms |
| PF | Peak Flow | ml s$^{-1}$ |
| SI | Stroke Index (SV divided by BSA) | ml m$^{-2}$ |
| SpO$_2$ | Saturation of Arterial Oxygen | % |
| STR | Systolic Time Ratio or Systolic Time Interval | — |
| SV | Stroke Volume | Ml |
| SVR | Systemic Vascular Resistance (using CO) | MmHg min L$^{-1}$ |
| SVRI | Systemic Vascular Resistance (using CI) | MmHg min L$^{-1}$ m$^2$ |
| SSRI | Systemic Vascular Resistance (using SI) | MmHg ml$^{-1}$ m$^2$ |
| TFC | Thoracic Fluid Contents = 1/$Z_0$ | k$\Omega^{-1}$ |
| TFI | Thoracic Fluid Index, equals $Z_0$ | $\Omega$ |
| VEPT | Volume of Electrically Participating Tissue | Ml |
| Z | Impedance = $Z_0 + \Delta Z$ | $\Omega$ |
| $Z_0$ | Base Impedance (averaged), equals TFI | $\Omega$ |
| $\Delta Z$ | Delta Z, dynamic component of impedance Z | $\Omega$ |

APPENDIX II

ICG MODULE PATIENT DATA COMMUNICATION PROTOCOL

| Data | DPR address | Description |
|---|---|---|
| CO (L * min$^{-1}$) | 7F50 | CO * 1000 |
| CI (L * min$^{-1}$ * m$^{-2}$) | 7F52 | CI * 1000 |
| SI (ml * m$^{-2}$) | 7F54 | SI * 10 |
| SV (ml) | 7F56 | SV * 10 |
| SVR (mmHg * min * L$^{-1}$) | 7F58 | |
| SVRI (mmHg * min * L$^{-1}$ * m$^2$) | 7F5A | |

APPENDIX II-continued

ICG MODULE PATIENT DATA COMMUNICATION PROTOCOL

| Data | DPR address | Description |
| --- | --- | --- |
| HR (bpm) | 7F5C | |
| MAP (mmHg) | 7F5E | |
| TFC ($\Omega^{-1}$) | 7F60 | TFC * 1000 |
| IC ($\sec^{-1}$) | 7F62 | IC * 10000 |
| ACI ($\sec^{-2}$) | 7F64 | ACI * 1000 |
| LCW (kg * m) | 7F66 | LCW * 100 |
| LCWI (kg * m * $m^{-2}$) | 7F68 | LCWI * 100 |
| PEP (ms) | 7F6A | |
| LVET (ms) | 7F6C | |
| STR | 7F6E | STR * 100 |
| RR (bpm) | 7F70 | |
| SSRI (mmHg * $ml^{-1}$ * $m^2$) | 7F72 | SSRI * 10 |
| LSWI (g * m * $m^{-2}$) | 7F74 | LSWI * 10 |
| EF (%) | 7F76 | |
| Program_ver_hundredth | 7F78 | 0.0X |
| Program_ver_tenth | 7F7A | 0.X0 |
| Program_ver_ones | 7F7C | X.00 |
| VEPT | 7F92 | Milliliters |
| Ideal Weight | 7F94 | Kilograms * 100 |
| BSA | 7F96 | BSA ($m^2$) * 100 |

What is claimed is:

1. Cardiac output measuring apparatus, comprising:
   a stimulation source adapted to produce a stimulation current;
   a first interface adapted to receive;
   (i) first signals from a first signal source, said first signals being related at least in part to said stimulation current; and
   (ii) second signals from a second signal source, said second signals being useful in the determination of cardiac output;
   said first interface further comprising a multiplexer adapted to selectively multiplex individual ones of said second signals;
   a selection apparatus adapted to arbitrate between individual ones of said second signals based on relative attributes of said second signals; and
   a second interface adapted to at least provide output data to a monitoring device.

2. The apparatus of claim 1, further comprising data processing apparatus, said processing apparatus being adapted to process at least a portion of said first and second signals to generate said output data.

3. The apparatus of claim 2, wherein said data processing apparatus comprises:
   at least one analog-to-digital converter adapted to convert at least said first signals from the analog domain to the digital domain;
   a digital processor, operatively coupled to said at least one converter, adapted to process said digital domain signals.

4. The apparatus of claim 3, wherein said digital processor comprises a digital signal processor (DSP) with computer program running thereon.

5. The apparatus of claim 4, wherein said DSP comprises a pipelined processor core with arithmetic logic unit (ALU) which is optimized for at least one arithmetic operation.

6. The apparatus of claim 4, wherein said computer program comprises a program adapted to identify at least one fiducial point within at least said first signals using a wavelet transform.

7. The apparatus of claim 4, wherein said first signals comprise an impedance waveform, said second signals comprise ECG signals, and said computer program is adapted to identify at least one fiducial point within each of said impedance waveform and said ECG signals.

8. The apparatus of claim 3, further comprising a microprocessor, said microprocessor being configured to control at least a portion of the operation of said cardiac output measuring apparatus and said third interface.

9. The apparatus of claim 8, wherein said microprocessor includes a computer program adapted to generate said output data according to at least one data communication protocol.

10. The apparatus of claim 3, further comprising signal filtering apparatus adapted to filter at least a portion of said first and second signals before processing by said processing apparatus.

11. The apparatus of claim 10, further comprising demodulator apparatus adapted to demodulate said filtered first signals prior to conversion thereof to the digital domain.

12. The apparatus of claim 3, further comprising apparatus adapted to measure the difference in at least two of said first signals, said difference being compared to a first predetermined value to evaluate the electrical continuity of at least one of the electrical terminals associated with said first signal source.

13. The apparatus of claim 12, wherein said apparatus adapted to measure the difference comprises a computer program running on said digital processor.

14. The apparatus of claim 1, wherein said second interface further comprises a network interface device adapted to facilitate transmission of said output data to said monitoring device over a data network.

15. The apparatus of claim 1, wherein said second interface comprises a wireless interface adapted to transmit said output data to said monitoring device over a wireless data link.

16. The apparatus of claim 15, wherein said second interface comprises a radio-frequency (RF) data link.

17. The apparatus of claim 15, wherein said second interface comprises an infra-red data link.

18. The apparatus of claim 15, wherein said monitoring device comprises a personal electronic device (PED) adapted to store at least a portion of said output data therein.

19. The apparatus of claim 1, wherein said second source comprises a plurality of sources of ECG signals.

20. The cardiac output measuring apparatus of claim 1, wherein said relative attributes are selected from the group consisting of:
   (1) R-wave magnitude;
   (2) QR interval difference; and
   (3) RR interval difference.

21. A method of determining the cardiac output of a living subject, comprising:
   generating an electrical current;
   applying said electrical current to at least a portion of said living subject;
   measuring an impedance waveform generated by said electrical current passing through said living subject;
   obtaining a cardiographic waveform from said subject during at least a portion of said act of measuring, said act of obtaining further comprising selecting one or more of a plurality of electrocardiographic (ECG) waveform inputs based on relative attributes of individual ones of said ECG waveform inputs;
   converting at least a portion of said impedance and cardiographic waveforms to the digital domain;
   removing at least one of respiration and motion artifact from at least one of said impedance and cardiographic waveforms;

determining stroke volume from the measured voltage; and determining cardiac output based at least in part on said stroke volume.

22. The method of claim 21, wherein the act of determining stroke volume comprises determining ventricular ejection time (VET) and the derivative of impedance, and calculating stroke volume based at least in part thereon.

23. The method of claim 22, wherein the act of determining cardiac output comprises multiplying stroke volume and cardiac rate.

24. The method of claim 21, wherein said act of determining stroke volume comprises detecting at least one fiducial point within said impedance waveform using a wavelet transform.

25. The method of claim 21, wherein said act of selecting comprises evaluating the signal quality of each waveform based on at least R-wave signal amplitude.

26. The method of claim 25, wherein said R-wave signal amplitude is determined by:
identifying a first R point value;
subtracting the previous local minimum point value.

27. The method of claim 26, further comprising:
summing the amplitudes of those R points found in a predetermined time window which includes said first R point value; and
averaging said summed amplitudes to determine a mean R wave signal amplitude.

28. The method of claim 21, further comprising determining cardiac rate at least in part from said one selected ECG waveform.

29. The method of claim 21, further comprising outputting said stroke volume and/or said cardiac output determinations to a monitoring device according to a communications protocol.

30. The method of claim 21, further comprising outputting said stroke volume and/or said cardiac output determinations via a network interface to a remote monitoring device.

31. Yoke apparatus adapted to measure cardiac output in a living subject, comprising:
a stimulation source adapted to produce a stimulation current;
a first interface adapted to receive;
  (i) first signals from at least one electrodes, said first signals being related to the thoracic impedance of said subject resulting from the application of said stimulation current thereto; and
  (ii) second signals from at least one electrode, said second signals being related to the ECG of said subject;
at least one digital processor adapted to process at least one of said first and second signals, said at least one digital processor having at least one computer program running thereon, said at least one computer program comprising three modules, said three modules comprising:
  (i) an initialization module;
  (ii) an operating module; and
  (iii) a processing module; and
a second interface adapted to at least provide output data to a monitoring device;
wherein said yoke apparatus is adapted to be physically separable from said monitoring device.

32. The yoke apparatus of claim 31, further comprising:
at least one analog-to-digital converter, said at least one converter adapted to convert said first and second signals to the digital domain for processing.

33. The yoke apparatus of claim 32, wherein said at least one computer program is further adapted to detect a plurality of fiducial points with at least said first signals.

34. The yoke apparatus of claim 33, wherein said detection of said fiducial points is accomplished using discrete wavelet transforms.

35. The yoke apparatus of claim 32, wherein said wireless interface comprises a Wireless Medical Telemetry Service compliant radio frequency (RF) interface.

36. The yoke apparatus of claim 32, further comprising an outer housing of molded construction, wherein said second interface comprises a multi-pin electrical connector.

37. The yoke apparatus of claim 32, wherein said first interface comprises a wireless data interface.

38. The yoke apparatus of claim 37, wherein said cardiac data comprises cardiac output (CO) data.

39. The yoke apparatus of claim 31, wherein said second interface comprises a wireless interface adapted to transfer a plurality of data bytes between said yoke and said monitoring device.

40. The yoke apparatus of claim 31, wherein said second interface comprises a LAN network card adapted to transfer data between said yoke and at least one remote network node.

41. The yoke apparatus of claim 31, wherein said second interface is adapted to transmit said output data as a plurality of data packets.

42. The yoke apparatus of claim 31, wherein said second interface further comprises at least one power terminal adapted to receive electrical power from said monitoring device.

43. The yoke apparatus of claim 31, further comprising a microprocessor and data storage device, said microprocessor, data storage device, and said at least one digital processor being in data communication, said microprocessor at least controlling the transfer of data between said yoke apparatus and said monitoring device via said second interface.

44. The yoke apparatus of claim 31, wherein said first interface comprises a wireless data interface.

45. The yoke apparatus of claim 31, further comprising a third interface, said third interface being adapted to receive data from a processing device, said processing device being adapted to determine at least one physical parameter of said subject.

46. The yoke apparatus of claim 31, further comprising a third interface, said third interface being adapted to transfer cardiac data to a processing device, said processing device being adapted to determine at least one physical parameter.

47. The yoke apparatus of claim 31, wherein any one of said three software modules can be downloaded independent of the other two modules.

48. Cardiac output measuring apparatus, comprising:
a stimulation source adapted to produce a stimulation current;
a first interface adapted to receive;
  (i) first signals from a first signal source, said first signals being related at least in part to said stimulation current; and
  (ii) second signals from a plurality of second signal sources, said second signals being useful in the determination of cardiac output;

said first interface further adapted to select at least one of said plurality of second signal sources based on relative attributes between individual ones of signals received from said plurality of second signal sources; and a second interface adapted to at least provide output data to a monitoring device.

49. Cardiac output measuring apparatus, comprising:

a stimulation source adapted to produce a stimulation current;

a first interface adapted to receive;
  (i) first signals from a first signal source, said first signals being related at least in part to said stimulation current; and
  (ii) second signals from a second signal source, said second signals being useful in the determination of cardiac output from a living subject;

a second interface adapted to at least provide output data to a monitoring device; and a computer program adapted to identify at least one fiducial point within at least said first signals using only additions and multiplications of real numbers.

50. ICG module apparatus, comprising:

a first interface adapted to receive impedance and ECG signals from a living subject, said first interface adapted to select individual ones of said ECG signals based on relative attributes analyzed between said individual ones of said ECG signals;

at least one filtration element adapted to filter at least portions of at least one of said impedance and ICG signals to create filtered signals;

at least one ADC adapted to convert at least a portion of said filtered signals to the digital domain;

a first processor having a computer program running thereon and adapted to at least control input and output functions of said module;

a second processor in data communication with said at least one ADC and having algorithms running thereon adapted to process said digital domain data to produce an output; and a second interface operatively coupled to said second processor and adapted to provide said output to an external device.

51. The apparatus of claim 50, further comprising at least one DAC in data communication with said second processor and adapted to convert said output to an analog form before delivery to said second interface.

52. Cardiac output measuring apparatus having a selectively reconfigurable software architecture, the apparatus comprising:

a stimulation source adapted to produce a stimulation current;

a first interface adapted to receive;
  (i) first signals from a first signal source, said first signals being related at least in part to said stimulation current; and
  (ii) second signals from a second signal source, said second signals being useful in the determination of cardiac output; and at least one digital processor adapted to process said first and second signals, said at least one digital processor having at least one computer program running thereon, said at least one computer program comprising three functional and substantially independent software modules; and a second interface adapted to at least provide output data to a monitoring device;

wherein any of said three software modules can be selectively reconfigured via download to said apparatus substantially independent of the other two modules.

53. The cardiac output measuring apparatus of claim 52, wherein said three modules comprise: (i) an initialization module; (ii) an operating module; and (iii) a processing module; and wherein:

said initialization module comprises a real-time, memory-resident, substantially event driven program adapted to monitor at least process scheduling, input and output, and inter-process communication functions within said apparatus;

said operating module is adapted to control interrupts, internal memory, stack pointer, and initial program counter functions; and said processing module is configured to execute at least one bioimpedance determination algorithm.

* * * * *